United States Patent
Randolph

(10) Patent No.: US 11,225,516 B2
(45) Date of Patent: *Jan. 18, 2022

(54) TRANSITION ANALYSIS METHOD FOR CHROMATOGRAPHY COLUMN QUALIFICATION

(71) Applicant: Janssen Biotech, Inc., Horsham, PA (US)

(72) Inventor: Paul Randolph, Malvern, PA (US)

(73) Assignee: JANSSEN BIOTECH, INC., Horsham, PA (US)

(*) Notice: Subject to any disclaimer, the term of this patent is extended or adjusted under 35 U.S.C. 154(b) by 14 days.

This patent is subject to a terminal disclaimer.

(21) Appl. No.: 16/389,146

(22) Filed: Apr. 19, 2019

(65) Prior Publication Data

US 2019/0321752 A1 Oct. 24, 2019

Related U.S. Application Data

(60) Provisional application No. 62/660,340, filed on Apr. 20, 2018.

(51) Int. Cl.
| | |
|---|---|
| *C07K 16/24* | (2006.01) |
| *G01N 30/56* | (2006.01) |
| *G01N 30/86* | (2006.01) |
| *B01D 15/20* | (2006.01) |
| *B01D 15/36* | (2006.01) |
| *B01D 15/38* | (2006.01) |
| *C07K 1/18* | (2006.01) |
| *C07K 1/22* | (2006.01) |
| *B01D 15/16* | (2006.01) |
| *G01N 35/00* | (2006.01) |

(52) U.S. Cl.
CPC .......... *C07K 16/244* (2013.01); *B01D 15/166* (2013.01); *B01D 15/20* (2013.01); *B01D 15/206* (2013.01); *B01D 15/362* (2013.01); *B01D 15/363* (2013.01); *B01D 15/3809* (2013.01); *C07K 1/18* (2013.01); *C07K 1/22* (2013.01); *C07K 16/241* (2013.01); *G01N 30/56* (2013.01); *G01N 30/8665* (2013.01); *G01N 35/00623* (2013.01); *C07K 2317/24* (2013.01); *C07K 2317/31* (2013.01); *C07K 2317/565* (2013.01); *G01N 2030/562* (2013.01)

(58) Field of Classification Search
CPC .............................................. G01N 2030/889
See application file for complete search history.

(56) References Cited

U.S. PATENT DOCUMENTS

| | | |
|---|---|---|
| 4,399,216 A | 8/1983 | Axel et al. |
| 4,634,665 A | 1/1987 | Axel et al. |
| 4,656,134 A | 4/1987 | Ringold |
| 4,956,288 A | 9/1990 | Barsoum |
| 5,122,464 A | 6/1992 | Wilson et al. |
| 5,149,636 A | 9/1992 | Axel et al. |
| 5,168,062 A | 12/1992 | Stinski |
| 5,179,017 A | 1/1993 | Axel et al. |
| 5,266,491 A | 11/1993 | Nagata |
| 5,385,839 A | 1/1995 | Stinski |
| 5,580,734 A | 12/1996 | Treco et al. |
| 5,641,670 A | 6/1997 | Treco et al. |
| 5,733,761 A | 3/1998 | Treco |
| 5,770,359 A | 6/1998 | Wilson et al. |
| 5,827,739 A | 10/1998 | Wilson et al. |
| 6,171,825 B1 | 1/2001 | Chan |
| 6,936,441 B2 | 8/2005 | Reiter |
| 8,410,928 B2 | 4/2013 | Ganguly |
| 8,895,709 B2 | 11/2014 | Hickman |
| 9,047,438 B2 | 6/2015 | Belousov et al. |
| 9,518,082 B2 | 12/2016 | Allison |
| 2007/0021277 A1 | 1/2007 | Kuo |
| 2007/0215548 A1 | 9/2007 | Zhou |
| 2008/0000904 A1 | 1/2008 | Vovan |
| 2011/0147312 A1 | 6/2011 | Cunnien |
| 2013/0281672 A1* | 10/2013 | Belousov ........... G01N 30/8665 530/387.7 |

FOREIGN PATENT DOCUMENTS

| | | |
|---|---|---|
| WO | 2007077217 | 7/2007 |
| WO | 2007117490 A2 | 10/2007 |

(Continued)

OTHER PUBLICATIONS

US 5,733,746 A, 03/1998, Treco (withdrawn)
Bork et al. "online integrity monitoring in the Protein A step of mAb production processes-increasing reliability and process robustness" (Biotechnol. Prog., 2014, vol. 30, No. 2, p. 383-390) (Year: 2014).*
Bork, et al., "Online Integrity monitoring in the Protein A step of mAb Production Processes-increasing reliability and process robustness", Biotechnology Progress, vol. 30, No. 2, pp. 383-390, (Jan. 2014).
International Search Report dated Aug. 8, 2019 in International Patent Application No. PCT/US2019/028349.
U.S. Appl. No. 16/389,055, Andrew M. Schechter, filed Apr. 19, 2019, Pending.
U.S. Appl. No. 16/389,114, Vickie Y. Kim, filed Apr. 19, 2019, Pending.
Boshart, et al., "A very strong enhancer is located upstream of an immediate early gene of human cytomegalovirus." Cell, vol. 41, No. 521-530, (1985).

(Continued)

*Primary Examiner* — Ryan B Huang
(74) *Attorney, Agent, or Firm* — Riverside Law LLP

(57) ABSTRACT

A method of operating a chromatography column is described. This method involves collecting column outlet signal and accumulated flow parameters at two or more intervals of at least one mobile phase transition front during operation of the chromatography column comprising column packing. A model gamma cumulative distribution curve is calculated based on the collected column outlet signal and accumulated flow parameters for the at least one mobile phase transition front. A height equivalent theoretical plate (HETP) value is calculated for the at least one mobile phase transition front using parameters of the model gamma cumulative distribution curve and the quality of the chromatography column packing is assessed based on the calculated HETP value.

17 Claims, 21 Drawing Sheets

(56) References Cited

FOREIGN PATENT DOCUMENTS

| | | |
|---|---|---|
| WO | 2009094203 A2 | 7/2009 |
| WO | 2018024770 | 2/2018 |

OTHER PUBLICATIONS

Cullen, et al., "Functional analysis of the transcription control region located within the avian retroviral long terminal repeat.", Molec. Cell. Biol., vol. 5, pp. 438-447 (1985).

Alt, et al., "Selective multiplication of dihydrofolate reductase genes in methotrexate-resistant variants of cultured murine cells.", J. Biol. Chem., vol. 25, No. 253, pp. 1357-1370 (1978).

Dolinar, et al., "A Guide to Follow-on Biologics and Biosimilars With a Focus on Insulin." Endocrine Practice, vol. 24, No. 2, pp. 195-204, (Feb. 2018).

Gossen, et al., "Tight control of gene expression in mammalian cells by tetracycline-responsive promoters.", Proc. Natl. Acad. Sci. USA, vol. 89, pp. 5547-5551 (1992).

Kunert, et al., "Advances in recombinant antibody manufacturing." Appl Microbiol Biotechnol., vol. 100, No. 8, pp. 3451-3461, (2016).

Larson, et al., "Use of Process Data to Assess Chromatographic Performance in Production-Scale Protein Purification 10 Columns,", Biotechnol. Prog., vol. 19, pp. 485-492 (2003).

Page, et al., "High level expression of the humanized monoclonal antibody Campath-1H in Chinese hamster ovary cells." Biotechnology, vol. 9, pp. 64-68 (1991).

Sprague, et al., "Expression of a recombinant DNA gene coding for the vesicular stomatitis virus nucleocapsid protein.", J. Virol., vol. 45, pp. 773-781 (1983).

Van Deemter, et al.,"Longitudinal Diffusion and Resistance to Mass Transfer as Causes of Nonideality in Chromatography,", Chem. Engng. Sci. vol. 5, pp. 271-289, (1956).

Gritti, et al., "The rationale for the optimum efficiency of columns packed with new 1.9 μm fully porous Titan-C18 particles—A detaled investigation of the intra-particle diffusivity", Journal of Chromatography A., vol. 1355, pp. 164-178, (Jun. 2014).

Jayapal et al., "Recombinant protein theo rapeutics from CHO cells-20 years and counting", 2007, Chern Eng Prog., 103:40-47.

Notice of Allowance dated Mar. 26, 2021 for U.S. Appl. No. 16/389,114 (pp. 1-8).

\* cited by examiner

TRANSITION ANALYSIS METHOD FOR CHROMATOGRAPHY COLUMN QUALIFICATION

CROSS REFERENCE TO RELATED APPLICATION

This application claims priority to U.S. Provisional Application No. 62/660,340, filed Apr. 20, 2018, which is incorporated herein by reference in its entirety.

FIELD OF THE INVENTION

The present invention relates to a method of chromatography column qualification.

BACKGROUND OF THE INVENTION

Column chromatography is an important technique used in purification processes to produce therapeutic proteins. The performance of columns must be maintained as the process is scaled-up from the bench top to manufacturing plants and throughout column lifetimes. Difficulties in column evaluation procedures, potential changes to the integrity of packed beds, and logistics can arise as the column diameter, equipment, and buffer consumption increases to scale up the process.

A current method for chromatography column qualification calculates Height Equivalent to Theoretical Plates (HETP), a measure of dispersion following a pulse injection, by estimating the mean from the peak maximum and the standard deviation from the width of the peak at half height. The primary limitation of this method is that it does not provide an accurate measure of dispersion (i.e., HETP) when the peak shape deviates from a Gaussian distribution. In order to compensate for the lack of sensitivity, a second measurement, Asymmetry, is utilized to assess peak skewness. This measure compares the leading and tailing peak width at 10% of the maximum peak height. The limitations of this approach result in a lack of sensitivity to changes in column performance, and often results in the repacking or conditioning of a column, while column performance is actually acceptable. Other strategies for column qualification have been reported. These strategies include using Gaussian or non-Gaussian distributions to model in process transitions (see e.g., Larson, et al., "Use of Process Data to Assess Chromatographic Performance in Production-Scale Protein Purification Columns," *Biotechnol. Prog.* 19:485-492 (2003) and U.S. Pat. No. 9,047,438 to Belousov et al., and U.S. Pat. No. 8,410,928 to Ganguly). The Gaussian approaches have the same limitations in sensitivity as noted supra for the injection method and the reported non-Gaussian approaches require complex calculations.

An improved qualification procedure with greater sensitivity and more rationally defined limits is needed to monitor changes in chromatography column performance during repeated operation and evaluate the effectiveness for which the column will perform over its lifetime. The present invention is directed at overcoming this deficiency in the art.

SUMMARY OF THE INVENTION

The embodiments of the invention are defined, respectively, by the independent and dependent claims appended hereto, which for the sake of brevity are incorporated by reference herein. Other embodiments, features, and advantages of the various aspects of the invention are apparent from the detailed description below taken in conjunction with the appended drawing figures.

In certain embodiments, the present invention provides a method of operating a chromatography column. This method involves collecting column outlet signal and accumulated flow parameters at two or more intervals of at least one mobile phase transition front during a first operation of the chromatography column comprising column packing. This method further involves determining a model gamma cumulative distribution curve based on the collected column outlet signal and accumulated flow parameters for the at least one mobile phase transition front using Formula Ia for a rising transition front or Formula Ib for a falling transition front, $$C = 1 - \frac{1}{r(k)} \gamma\left(k, \frac{V - V_i}{\theta}\right) \quad \text{Formula Ia}$$

or $$C = \frac{1}{r(k)} \gamma\left(k, \frac{V - V_i}{\theta}\right) \quad \text{Formula Ib}$$

wherein C is column outlet signal for a given V, V is the accumulated flow divided by the column volume, and k, θ, and $V_i$ are the shape, scale and offset parameters used to define the curve. The height equivalent theoretical plate (HETP) value is calculated for the at least one mobile phase transition front using Formula II and the model gamma cumulative distribution curve parameters of k, θ, and $V_i$, $$HETP = \frac{\sigma^2}{\mu^2} L \quad \text{Formula II}$$

where
$\mu = k\theta + V_i$,
$\sigma = \sqrt{k\theta^2}$, and
L=column length

The quality of the chromatography column packing is assessed based on the calculated HETP value. Based on this assessment, the chromatography column is reused, conditioned, replaced, or repacked.

A new method for assessing column integrity, referred to herein as Gamma Distribution Transition Analysis (GDTA), has been developed. The new method uses a mathematical model to fit a curve through mobile phase transition front data that is generated during regular process steps of column operation. Model curve parameters are then utilized to calculate the dispersion across the column bed as a measure of column quality. Mobile phase transition fronts arise from discrete steps within the chromatography purification process where process buffers/wash solutions with different properties, such as conductivity, pH, and/or buffer components are used. The method can generally be applied to any one or more mobile phase transition fronts generated during normal column processing.

A primary advantage of the GDTA method is that it provides a more sensitive gauge of dispersion across the column bed than the Gaussian HETP estimation method. By using GDTA, it is no longer necessary to measure asymmetry, as the GDTA model correctly measures dispersion from the curve fit. Additionally, the use of the gamma distribution function facilitates ease of analysis of frontal transitions when compared to alternative non-gaussian methods previously reported. The use of mobile phase transitions already present in a chromatography process avoids the need for extra offline processing steps. Furthermore, in many cases, historical data allows for establishment of historical ranges of column efficiency prior to implementation. Finally, the GDTA method can be automated to ensure consistent application.

In certain embodiments, the present invention provides a method of operating a chromatography column, said method comprising:

collecting column outlet signal and accumulated flow parameters at two or more intervals of at least one mobile phase transition front during a first operation of the chromatography column comprising column packing;

determining a model gamma cumulative distribution curve based on the collected column outlet signal and accumulated flow parameters for the at least one mobile phase transition front using Formula Ia for a rising transition front or Formula Ib for a falling transition front, $$C = 1 - \frac{1}{\Gamma(k)} \gamma\left(k, \frac{V - V_i}{\theta}\right) \quad \text{Formula Ia}$$

or $$C = \frac{1}{\Gamma(k)} \gamma\left(k, \frac{V - V_i}{\theta}\right) \quad \text{Formula Ib}$$

wherein C is column outlet signal for a given V, V is the accumulated flow divided by the column volume, and k, θ, and $V_i$ are the shape, scale and offset parameters used to define the curve;

calculating a height equivalent theoretical plate (HETP) value for the at least one mobile phase transition front using Formula II and the model gamma cumulative distribution curve parameters of k, θ, and $V_i$, $$HETP = \frac{\sigma^2}{\mu^2} L \quad \text{Formula II}$$

wherein $\mu = k\theta + V_i$ $\sigma = \sqrt{k\theta^2}$

L=column length; and assessing quality of the chromatography column packing based on said calculated HETP value.

In certain embodiments, the present invention provides a method further comprising:

conditioning, replacing, or repacking the chromatography column based on said assessing.

In certain embodiments, the present invention provides a method further comprising:

collecting column outlet signal and accumulated flow parameters at two or more intervals of a corresponding mobile phase transition front during one or more subsequent uses of the chromatography column packing;

performing said determining and said calculating using the column outlet signal and accumulated flow parameters collected during each of the one or more subsequent uses of the chromatography column packing;

determining an HETP value of the chromatography column packing during each of said one or more subsequent uses based on said performing;

compiling a trend of the determined HETP values of the chromatography column packing of the two or more subsequent uses; and identifying a change in the quality of the chromatography column packing based on said compiled trend, wherein said conditioning, replacing or repacking the chromatography column is based on said identifying.

In certain embodiments, the present invention provides a method, wherein an increase in the HETP value of the chromatography column packing in the one or more subsequent uses of said column packing as compared to the HETP value of the chromatography column packing in one or more earlier uses of said column packing identifies a decrease in quality of the chromatography column packing.

In certain embodiments, the present invention provides a method, wherein column outlet signal and accumulated flow parameters of two or more different mobile phase transition fronts during said first operation of the column packing are collected, said method comprising:

performing said determining and calculating using the column outlet signal and accumulated flow parameters collected for each of the two or more different mobile phase transition fronts independently to calculate an HETP value for each of the two of more different mobile phase transition fronts;

assessing the quality of the chromatography column packing based on the two or more calculated HETP values, whereby said conditioning, replacing or repacking the chromatography column is based on said assessing.

In certain embodiments, the present invention provides a method, wherein the mobile phase transition front is generated by a change from a mobile phase containing a denaturing agent to a mobile phase containing a non-denaturing agent.

In certain embodiments, the present invention provides a method, wherein the mobile phase transition front is generated by a change from a mobile phase containing a non-denaturing agent to a mobile phase containing a denaturing agent.

In certain embodiments, the present invention provides a method, wherein the mobile phase transition front is generated by a change from an alkaline mobile phase condition to a more acidic mobile phase condition.

In certain embodiments, the present invention provides a method, wherein the mobile phase transition front is generated by a change from an acidic mobile phase condition to a more alkaline mobile phase condition.

In certain embodiments, the present invention provides a method, wherein the mobile phase transition front is generated by a change from organic solvent containing mobile phase to an aqueous mobile phase.

In certain embodiments, the present invention provides a method, wherein the mobile phase transition front is generated by a change from an aqueous mobile phase to an organic solvent containing mobile phase.

In certain embodiments, the present invention provides a method, wherein the column outlet signal is conductivity.

In certain embodiments, the present invention provides a method, wherein said determining comprises:

normalizing said collected column outlet signal of the mobile phase transition front by setting the minimum signal value to 0 and the maximum conductivity value to 1.

In certain embodiments, the present invention provides a method, wherein said collecting comprises:

adding a first mobile phase to the chromatography column containing said column packing;

adding a second mobile phase to the chromatography column containing said column packing, wherein said first and second mobile phases have different detectable column outlet signals; and collecting said column outlet signal and accumulated flow parameters at two or more intervals of the mobile phase transition between the first and second mobile phases.

In certain embodiments, the present invention provides a method, wherein the column outlet signal for the first and second mobile phases differ in signal by an amount exceeding the signal noise.

In certain embodiments, the present invention provides a method, wherein the column outlet signal and accumulated flow parameters are collected at various intervals throughout the entirety of the mobile phase transition front.

In certain embodiments, the present invention provides a method, wherein the chromatography column packing is selected from the group consisting of affinity chromatography packing material, ion exchange chromatography packing material, adsorption chromatography packing material, hydrophobic interaction chromatography packing material, metal chelate affinity chromatography packing material, size exclusion chromatography packing material, or molecular exclusion chromatography packing material.

BRIEF DESCRIPTION OF THE DRAWINGS

FIG. 1A is a graph showing an exemplary gamma distribution transition analysis curve fit to mobile phase transition data. FIG. 1B is a graph showing an exemplary gamma distribution transition analysis curve fit to mobile phase transition data with parameters from that curve used to calculate the height equivalent theoretical plate (HETP) as a measure of column efficiency.

DETAILED DESCRIPTION OF THE INVENTION

Figure 1A:
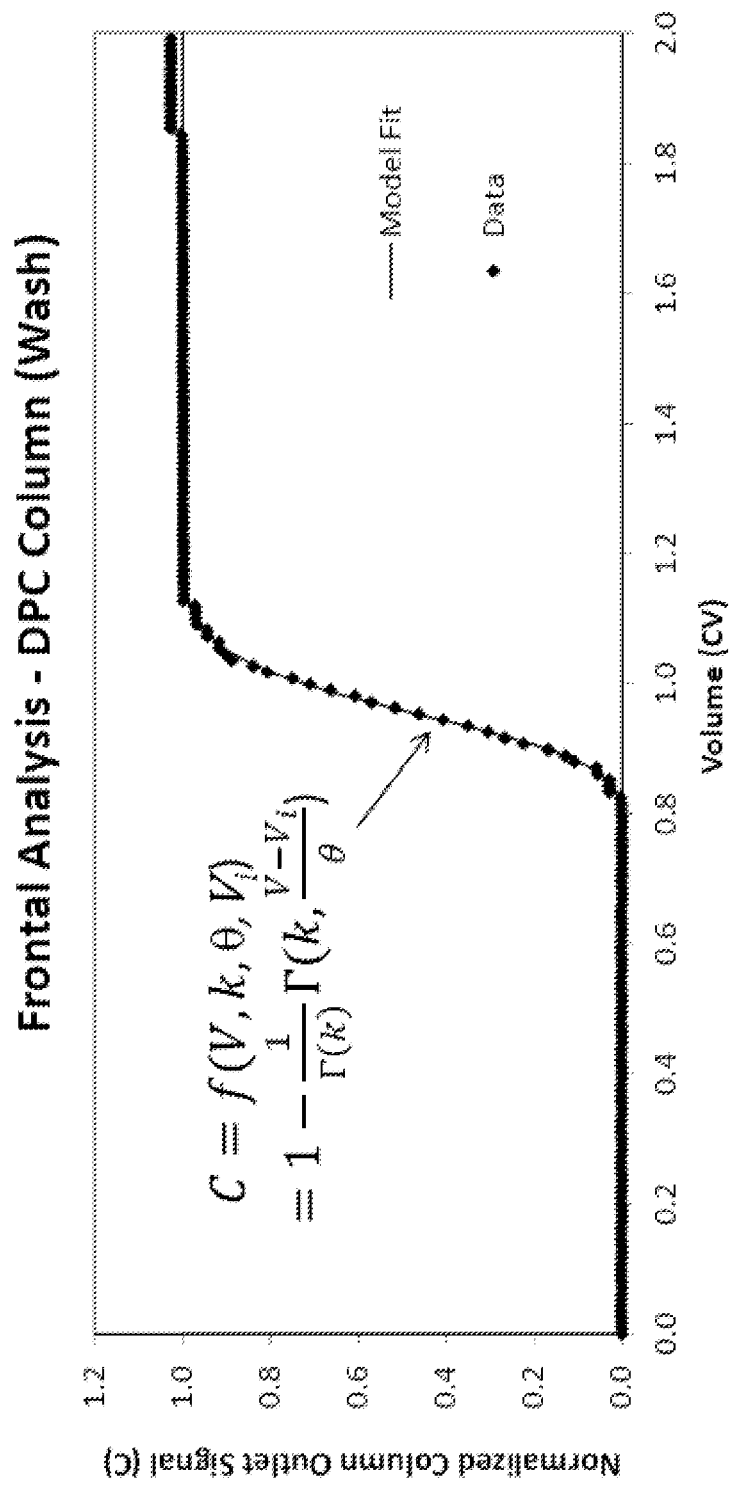
FIGS. 1A-1B show graphs of exemplary gamma distribution transition analysis curve fits.

The present disclosure relates to an improved qualification procedure for monitoring changes in packed chromatography column beds during repeated operation of the column. This method, independent of scale, provides a practical means to evaluate the effectiveness for which the column will perform throughout the column lifetime.

Chromatography column separation efficiency is often characterized using the theoretical plate model of chromatography. Using this approach, the chromatography column is perceived as consisting of a number of stages or theoretical plates. Each plate is the distance over which the sample components achieve equilibrium between the mobile and stationary phases (see Van Deemter, Zuiderweg and Klinkenberg, "Longitudinal Diffusion and Resistance to Mass Transfer as Causes of Nonideality in Chromatography," *Chem. Engng. Sci.* 5: 271-289 (1956), which is hereby incorporated by reference in its entirety). Column efficiency is measured by the number of theoretical plates in the column $N_p$, where more plates in the column means more equilibrations, less dispersion of chromatographic bands, narrower peaks, and better-quality separation. The higher the number of plates in a given column, the lower the plate height. Accordingly, column efficiency can also be measured by calculating plate height, which is referred to as "height equivalent to a theoretical plate" or HETP. Using this approach, the smaller the HETP value the higher the efficiency of column separation.

HETP is calculated by dividing by the length of chromatography column L by the number of theoretic plates $N_p$.

$$HETP = L/N_p$$

The number of theoretical plates that a column possesses has historically been determined by examining a chromatographic peak after a pulse injection using the following formula:

$$N_p = 5.54\left(\frac{t_R}{w_{1/2}}\right)^2$$

where $t_R$ is the retention time and $w_{1/2}$ is the peak width at half height. However, this approach does not provide an accurate measure of column efficiency when the peak shape used to calculate $N_p$ deviates from a Gaussian distribution. In order to compensate for this lack of sensitivity, a second measurement—Asymmetry—is used to assess peak skewness. This measure compares the leading and tailing peak width at 10% of the maximum peak height. As discussed supra, this model lacks sensitivity to detect changes in column performance.

The method described herein provides an alternative and more accurate measure of HETP that is based on gamma distribution over one or more mobile phase transition fronts that occur during routine chromatography column operation. Thus, the present disclosure is directed to a method of operating a chromatography column. This method involves collecting column outlet signal and accumulated flow parameters at two or more intervals of at least one mobile phase transition front during a first operation of the chromatography column containing column packing. This method further involves determining a model gamma cumulative distribution curve based on the collected column outlet signal and accumulated flow parameters for the at least one mobile phase transition front using Formula Ia for a rising transition front or Formula Ib for a falling transition front.

$$C = 1 - \frac{1}{\Gamma(k)}\gamma\left(k, \frac{V - V_i}{\theta}\right) \quad \text{Formula Ia}$$

or $$C = \frac{1}{\Gamma(k)}\gamma\left(k, \frac{V - V_i}{\theta}\right) \quad \text{Formula Ib}$$

In reference to Formula Ia and Formula Ib, C is column outlet signal for a given V, V is the accumulated flow divided by the column volume, and k, θ, and $V_i$ are the shape, scale and offset parameters used to define the curve. The height equivalent theoretical plate (HETP) value is calculated for the at least one mobile phase transition front using Formula II and the model gamma cumulative distribution curve parameters of k, θ, and $V_i$,
where $$HETP = \frac{\sigma^2}{\mu^2}L \quad \text{Formula II}$$

$\mu = k\theta + V_i$ $\sigma = \sqrt{k\theta^2}$, and

L=column length.

The quality of the chromatography column packing is assessed based on the calculated HETP value. Based on the assessment of column quality, the chromatography column is determined to be acceptable for subsequent use, or otherwise must be conditioned, replaced, or repacked.

The method of column qualification disclosed herein can be applied to any chromatography column. Exemplary chromatography columns include, without limitation, those used for liquid chromatography, high-performance liquid chromatography (HPLC), ion exchange chromatography, affinity chromatography, molecular exclusion, super critical fluid chromatography, gas chromatography, size exclusion chromatography, reverse phased chromatography, two-dimensional chromatography, fast protein (FPLC) chromatography, countercurrent chromatography, chiral chromatography, aqueous normal phase (ANP), mixed mode chromatography, and pseudo-affinity chromatography. Exemplary column packing material includes, without limitation, affinity chromatography packing material (e.g., protein A or protein G affinity chromatography packing material), ion exchange chromatography packing material (e.g., cation exchange (carboxymethyl resins), anion exchange (amino ethyl resins), and mixed-mode exchange chromatography packing material), adsorption chromatography packing material (e.g. silica gel or alumina packing material), hydrophobic interaction chromatography packing material (e.g. phenyl-sepharose, aza-arenophilic resins, or m-aminophenylboronic acid packing materials), metal chelate affinity chromatography packing material (e.g., Ni(II)- and Cu(II)-affinity material), size exclusion chromatography packing material (e.g., gel electrophoresis or capillary electrophoresis packing material), or molecular exclusion chromatography packing material (e.g., polystyrene).

The method described herein can be applied during routine chromatography column operation, e.g., during isolation, purification, or identification of chemical or biological entities in a sample. Such compounds may include, for example but without limitation, proteins (e.g., antibodies and fragments thereof), nucleic acids, carbohydrates, lipids, organic small molecules, inorganic small molecules, viruses, liposomes, and hybrids or variant forms of any such compounds.

In contrast to previous chromatography column qualification methods, which require the column be taken offline for testing, e.g., the pulse injection method, the method as described herein is carried out during routine column operation. The present method takes advantage of mobile phase process transitions involving process buffers and solutions having different properties, which occur during a routine column purification process.

In accordance with the method of the present invention, the "mobile phase" is the liquid phase in column chromatography that surrounds and moves through the stationary chromatography material of the chromatography column packing. During chromatography column operation, the composition and properties of the mobile phase often change with each process step, e.g., equilibration, washes, etc. Changes in the properties of the mobile phase can be detected and measured in the eluate, i.e., the mobile phase that is eluted from the column after passing through the stationary phase. As used herein, the "column outlet signal" is the signal of a physical or chemical property of the eluate from the mobile phase that is detected as the eluate elutes off the column. The physical or chemical property providing the column outlet signal can be any property, such as pH, conductivity, light absorption, fluorescence, charge, salt concentration, polarimetry, refractive index, electrochemical response, mass-to-charge ratio, etc. that can be measured using any typical chromatography detector. Chromatography detectors suitable for measuring the column outlet signal include, without limitation, a mass spectrometer, infrared spectrometer, visible spectrometer, ultraviolet spectrometer, Fourier transform infrared spectrometer, flame ionization detector, low angle laser light scattering detector, diode array detector, fluorescence spectrometer, pH detector, conductivity detector, electrochemical detector, and refractive index detector.

The column outlet signal is collected from the eluate. In addition, to collecting the column outlet signal, the "accumulated flow" is also collected. The "accumulated flow" is the total volume of fluid eluted from the column over time. This value is divided by the volume of the column to be expressed in units of column volumes.

A transition front is generated by the change in column outlet signal over the accumulated flow. A transition front arises from the sequential application of different mobile phases having one or more different properties (e.g., conductivity, pH, etc.) to a column. In accordance with the method described herein, the column outlet signal over the transition front can be normalized to have a maximum value of 1 and a minimum value of 0. As referred to herein, a "falling transition front" is a mobile phase transition where the starting mobile phase has a column outlet signal, e.g., conductivity, that is higher than the column outlet signal of the sequentially introduced mobile phase.

A "rising transition front" as used here is a mobile phase transition where the starting mobile phase has a column outlet signal, e.g., conductivity, that is lower than the column outlet signal of the sequentially introduced mobile phase.

A transition front is created by adding a first mobile phase to the chromatography column containing column packing to be qualified during the course of column operation.

At some time after the addition of the first mobile phase, e.g., as the first mobile phase begins to elute, a second mobile phase having a different detectable column outlet signal compared to the first mobile phase is added to the chromatography column containing the column packing. The transition front is detected by collecting column outlet signal and accumulated flow parameters at two or more intervals of the mobile phase as it transitions between the first and second mobile phases.

In one embodiment, the column outlet signal for the first and second mobile phases differ in signal by an amount exceeding the signal noise. In one embodiment, the difference in column outlet signal between the first and second mobile phases is 5% above the background signal noise. In another embodiment, the difference in column outlet signal between the first and second mobile phases is at least 10% above the background signal noise. In another embodiment, the difference in column outlet signal between the first and second mobile phases is at least 15% above the background signal noise.

In one embodiment, the column outlet signal detected over the transition front is conductivity. In this embodiment, the column outlet signal between the first and second mobile phases preferably differs by at least 1 μS/cm, by at least 10 μS/cm, by at least 100 μS/cm, by at least 1 mS/cm, or by greater than 1 mS/cm.

In another embodiment, the column outlet signal detected over the transition front is pH. In this embodiment, the column outlet signal between the first and second mobile phases preferably differs by at least 0.05 pH units, by at least 0.1 pH units, by at least 1 pH units, by at least 2 pH units, or by greater than 2 pH units.

In another embodiment, the column outlet signal detected over the transition front is UV-Vis absorbance. In this embodiment, the column outlet signal between the first and second mobile phases preferably differs by at least 0.01 absorbance unit, by at least 0.1 absorbance unit, by at least 0.5 absorbance unit, by at least 0.8 absorbance unit, or by more than 0.8 absorbance unit.

In another embodiment, the column outlet signal detected over the transition front is infrared absorbance. In this embodiment, the column outlet signal between the first and second mobile phases preferably differs by at least 1 percent transmittance, by at least 10 percent transmittance, by at least 20 percent transmittance, by at least 30 percent transmittance, or by more than 30 percent transmittance.

In one embodiment, the mobile phase transition front is generated by a change from a mobile phase containing a denaturing agent to a mobile phase containing a non-denaturing agent. In another embodiment, the mobile phase transition front is generated by a change from a mobile phase containing a non-denaturing agent to a mobile phase containing a denaturing agent.

In another embodiment, the mobile phase transition front is generated by a change from an alkaline mobile phase condition to a neutral or more acidic mobile phase condition. Alternatively, the mobile phase transition front is generated by a change from an acidic mobile phase condition to a neutral or more alkaline mobile phase condition.

In another embodiment, the mobile phase transition front is generated by a change from organic solvent containing mobile phase to an aqueous mobile phase. Alternatively, the mobile phase transition front is generated by a change from an aqueous mobile phase to an organic solvent containing mobile phase.

The column outlet signal and accumulated flow parameters are collected at various intervals over the course of the mobile transition front. Preferably, column outlet signal and accumulated flow parameters are collected over the course of the entire mobile transition front, from the minimum column outlet signal to the maximum column outlet signal or vice versa. In one embodiment, the column outlet signal and accumulated flow parameters are collected at irregular intervals, e.g., collected when a change in the column outlet signal is detected. In another embodiment, the column outlet signal and accumulated flow parameters are collected at regular timed intervals over the course of the entire mobile transition front. For example, in one embodiment, the column outlet signal and accumulated flow parameters are collected at 1 second intervals over the course of the entire mobile transition front. In another embodiment, the column outlet signal and accumulated flow parameters are collected at 5, 10, 15, 20, 25, 30, 35, 40, 45, 50, 55, or 60 second intervals over the course of the mobile transition phase.

In one embodiment, the column outlet signal data is normalized as described supra by setting the maximum value to 1 and the minimum value to 0 over the period of analysis. Flow is also converted to column volumes to standardize for comparison of data between different column packings. Using this data, the gamma cumulative distribution function ("CDF") is used to generate a curve that best fits the collected data points. The gamma CDF is determined by three values: shape parameter k; scale parameter θ (theta); and offset parameter $V_i$ using the following Formula I:

$$C = f(V, k, \theta, Vi) \qquad \text{Formula I}$$

In reference to Formula I, C is column outlet signal for a given V, Vis the accumulated flow divided by the column volume. Formula Ia, which is derived from Formula I, is used determine the gamma distribution function value along a rising transition front.

$$C = 1 - \frac{1}{\Gamma(k)} \gamma\left(k, \frac{V - V_i}{\theta}\right) \qquad \text{Formula Ia}$$

wherein
Γ is the upper incomplete gamma function, and
γ is the lower incomplete gamma function.

Alternatively, Formula Ib, which is also derived from Formula I, is used to determine the gamma distribution function value along a falling transition front.

$$C = \frac{1}{\Gamma(k)} \gamma\left(k, \frac{V - V_i}{\theta}\right) \qquad \text{Formula Ib}$$

FIG. 1A is a graph plotting exemplary normalized column outlet signal and column volume data collected over a column transition front. Formula Ia was used to generate the curve fit to the data.

The best fit gamma CDF parameters are determined by manipulating the values of k, θ, and $V_i$ to find the parameters that produce a model curve with the least sum of squares deviation from the data. This curve is fitted through the data points from the entire transition front to generate the best fit model. The k, θ, and $V_i$ parameters from this curve are utilized to calculate the number of plates $N_p$ in the column or the plate height, i.e., HETP, as indicators of column efficiency.

The number of plates $N_p$ is calculated based on the mean μ and variance $\sigma^2$ of the model curve. The mean and variance are derived from the curve as follows:

Mean, $\mu = k\theta + V_i$

Variance, $\sigma^2 = k\theta^2$

The number of plates is calculated based on the mean and variance as follows:

Number of plates, $N_p = \mu^2/\sigma^2$

The HETP is calculated as described supra based on the length of the column L in centimeters divided by the number of plate $N_p$, as follows.

$$HETP = \frac{L}{N_p} = \frac{\sigma^2}{\mu^2} \cdot L = \frac{k\theta^2 L}{(k\theta + V_i)}$$

Figure 1B:
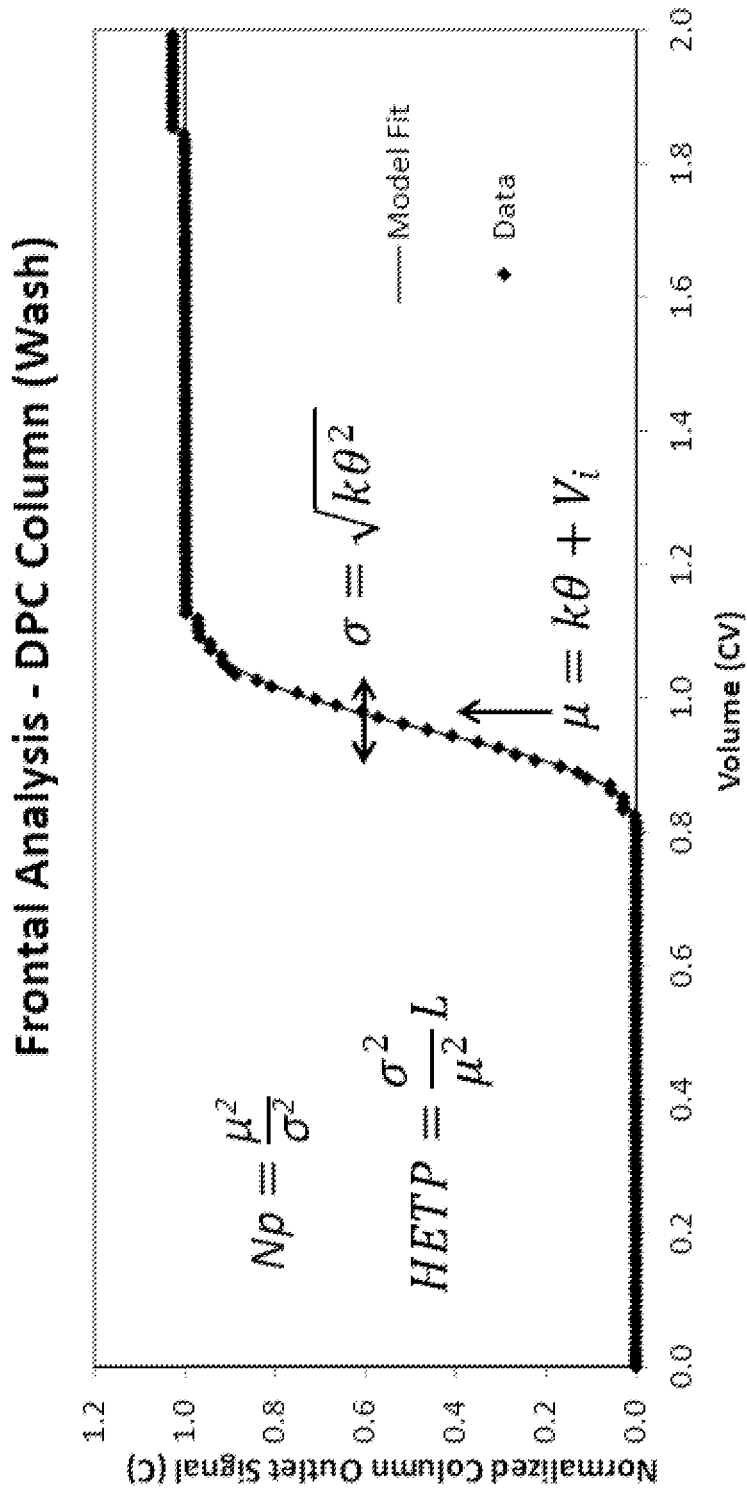

FIG. 1B shows the same graph as shown in FIG. 1A, with the mean L and variance σ2 parameters defined.

To evaluate the model fit to the data calculated as described herein, the mean ($V_m$), sum of squares (SS), and mode can also be determined. SS is a direct measure of the deviation of the model curve from the process data upon which it is derived. The $V_m$ value is a measure of the center point of the transition in units of column volumes. This value should be close to one as it typically takes one column volume for a buffer transition. Mean is not typically affected by the shape of the front. Mean values are used to check the automatic calculations for errors. For example, a low value might indicate a data collection error and may require further investigation to confirm the result. The mode corresponds to the volume where the rate of change is greatest. This will be equal to the mean when the transition curve is symmetrical. Typically, the transitions are skewed, and the mode is lower than the mean.

In addition to HETP, other factors that can be calculated from the k (shape) parameter include skewness ($\gamma_1$), which is a measure related to asymmetry, and kurtosis ($\gamma_2$), which is a measure of the peak sharpness. These factors can be used to identify changes in column performance.

$$\gamma_1 = \frac{2}{\sqrt{k}}$$

$$\gamma_2 = \frac{6}{k}$$

In accordance with the method described herein, the column outlet signal and accumulated flow parameters are collected for the same mobile transition phase each time the column process is run on the column to calculate HETP from the gamma CDF. Historical data generated by columns used for the same process step and same scale can also be retrieved and utilized to calculate HETP. The HETP data is compiled to identify trends in the HETP values of corresponding transitions during historical or current operations to identify upper and lower control limits of the HETP value. The control limits are the high and low values of HETP that define the range of acceptable HETP values, i.e., HETP values that correspond to acceptable column efficiency. These upper and lower control limits can be set based on statistical evaluation. For example, in one embodiment the upper and lower control limits are set by calculating the mean+/−2, 3, or 4 standard deviations. In one embodiment, the upper and lower control limits are set by calculating the mean+/−3 standard deviations as described in the Examples herein. In another embodiment, the upper and lower control limits can be set by calculating the confidence interval from the historical data. In one embodiment, the upper and lower control limits are set by calculating the 95%, 96%, 97%, or 98% confidence interval from the historical data. In another embodiment, the upper and lower control limits are set by calculating the 99% confidence interval from the historical data.

The upper and lower control limits are utilized to identify changes in column efficiency over time and use of the column. Typically, any increase in HETP that exceeds the upper control limit may be indicative of a decrease in column efficiency. If during routine column monitoring, an adverse trend in HETP is observed or the control limits are exceeded, the eluate product quality, column process performance, and/or impurity removal data should be evaluated to ensure product quality for the identified batch. Should any of the product quality or column performance fail the criteria set, appropriate corrective action, such as conditioning, repacking or replacing the column, and qualification should be performed prior to release for further use. Methods of conditioning a chromatography column to redistribute the packed bed will vary depending on the column being employed, but are well understood to those of skill in the art.

The monitoring of column performance during column operation can be based on one, or more than one, transition phases that are routinely included in a purification protocol. Preferably, monitoring is based on HETP values calculated based on gamma CDF for two, or three, or more transition phases during a purification protocol.

As noted infra, calculating HETP using the GDTA method as described herein to determine column performance can be based on historical data collected from columns used for the same process step and same scale. Data generated from a qualified reduced scale model of the process step can also be used for the evaluation. This allows for the evaluation of the quality of the column's performance as compared to the qualification data.

Factors such as flow rate (Van Deemter effect), potential buffer interactions and extra column volume can impact the results of the GDTA method as described herein and should be assessed in setting the control limits for GDTA. Transition fronts included in the GDTA preferably meet certain criteria such as both mobile phase column outlet signal measurements are on scale, the column outlet signal measurement difference between mobile phases is above the background signal noise, and interaction between mobile phase and resin is consistent and reproducible.

Common column evaluation criteria used for release and monitoring during use shall be determined by evaluating historical data specific to equipment and resin type. Examples of routine product quality and process performance measurements that can be used to evaluate the relationship between column qualification results and performance are listed in Table 1. Routine quality and process performance measurements used for evaluation are not limited to those listed in Table 1, but the list is meant to be a guideline and should be based on the specific requirements of the project and process step being evaluated. Specifications and acceptance criteria for product quality and process performance are project specific and will be determined based on process requirements.

TABLE 1

Routine Quality and Step Performance Measures

| Parameter | Analytical method |
| --- | --- |
| Pre-Elution Volume (CV) | |
| Elution Volume (CV) | |
| Step Yield | |
| Chromatographic Profile | Visual Inspection |
| Eluate Concentration | $A_{280}$ |
| Eluate Monomer | DW-SE-HPLC |
| Process Impurities | Various Assays |

The gamma distribution transition analysis method as described herein can be carried out in real-time during column operation. This method involves collecting, by a chromatography column qualification computing device, column outlet signal and accumulated flow parameters at two or more intervals of at least one mobile phase transition front during a first operation of the chromatography column comprising column packing; determining, by a chromatography column qualification computing device, a model gamma cumulative distribution curve based on the collected column outlet signal and accumulated flow parameters for the at least one mobile phase transition front using Formula Ia for a rising transition front or Formula Ib for a falling transition front.

$$C = 1 - \frac{1}{\Gamma(k)} \gamma\left(k, \frac{V-V_i}{\theta}\right) \quad \text{Formula Ia}$$

or $$C = \frac{1}{\Gamma(k)} \gamma\left(k, \frac{V-V_i}{\theta}\right). \quad \text{Formula Ib}$$

In reference to Formulas Ia and Ib, C is column outlet signal for a given V, V is the accumulated flow divided by the column volume, and k, θ, and $V_i$ are the shape, scale and offset parameters used to define the curve. This method further involves calculating, by a chromatography column qualification computing device, a height equivalent theoretical plate (HETP) value for the at least one mobile phase transition front using Formula II and the model gamma cumulative distribution curve parameters of k, θ, and $V_i$, $$HETP = \frac{\sigma^2}{\mu^2} L \quad \text{Formula II}$$

wherein $$S = k\theta + V_i$$

$$\sigma = \sqrt{k\theta^2}$$

L=column length.

The method further involves assessing, using a chromatography column qualification computing device, quality of the chromatography column packing based on said calculated HETP value. Based on this assessment, the chromatography column operator can determine whether the chromatography column can be reused, or needs to be replaced, repacked, or conditioned prior to the next column operation.

Figure 2:
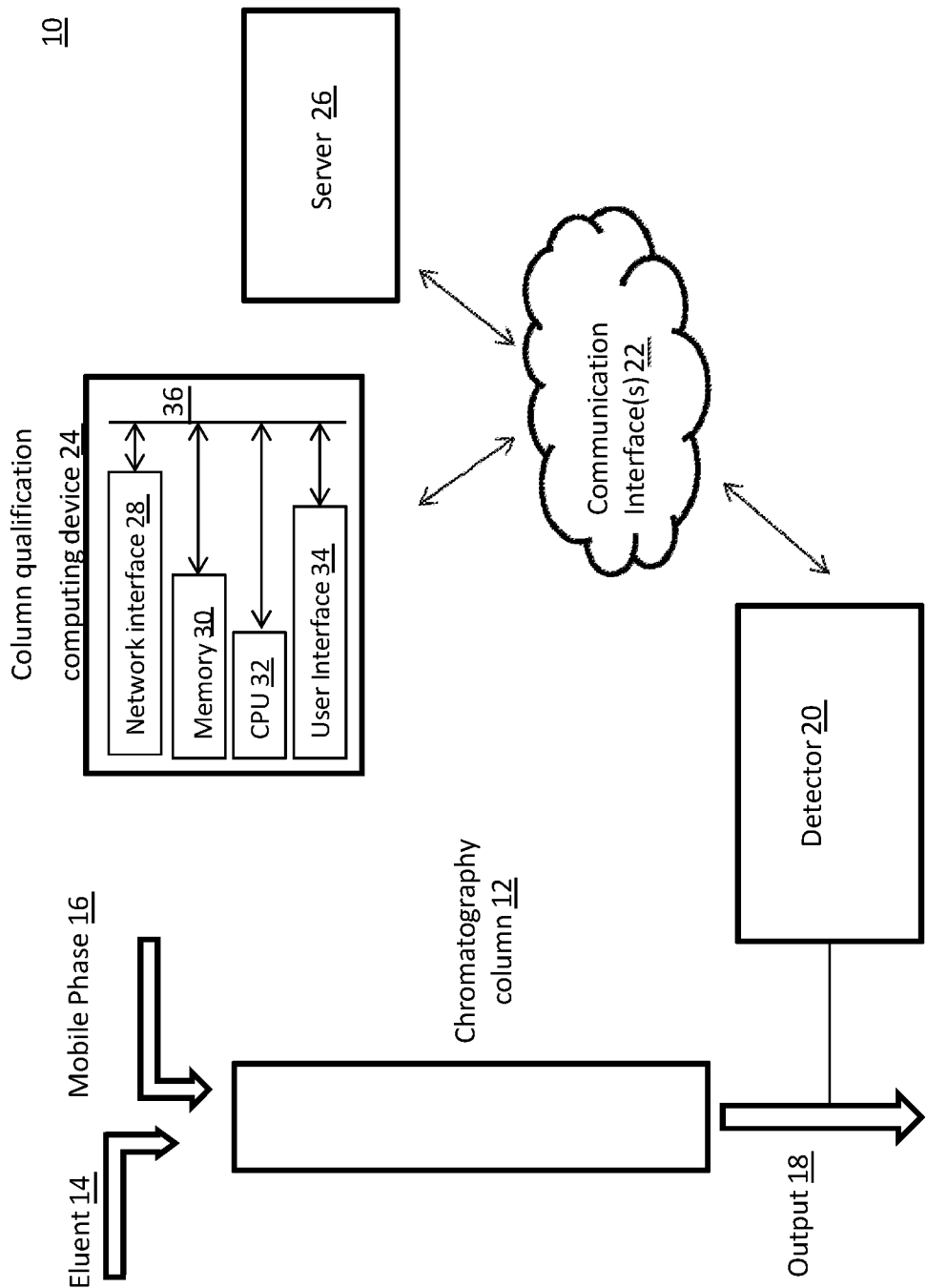
FIG. 2 is a diagram showing the chromatography column qualification system described herein.
Figure 3:
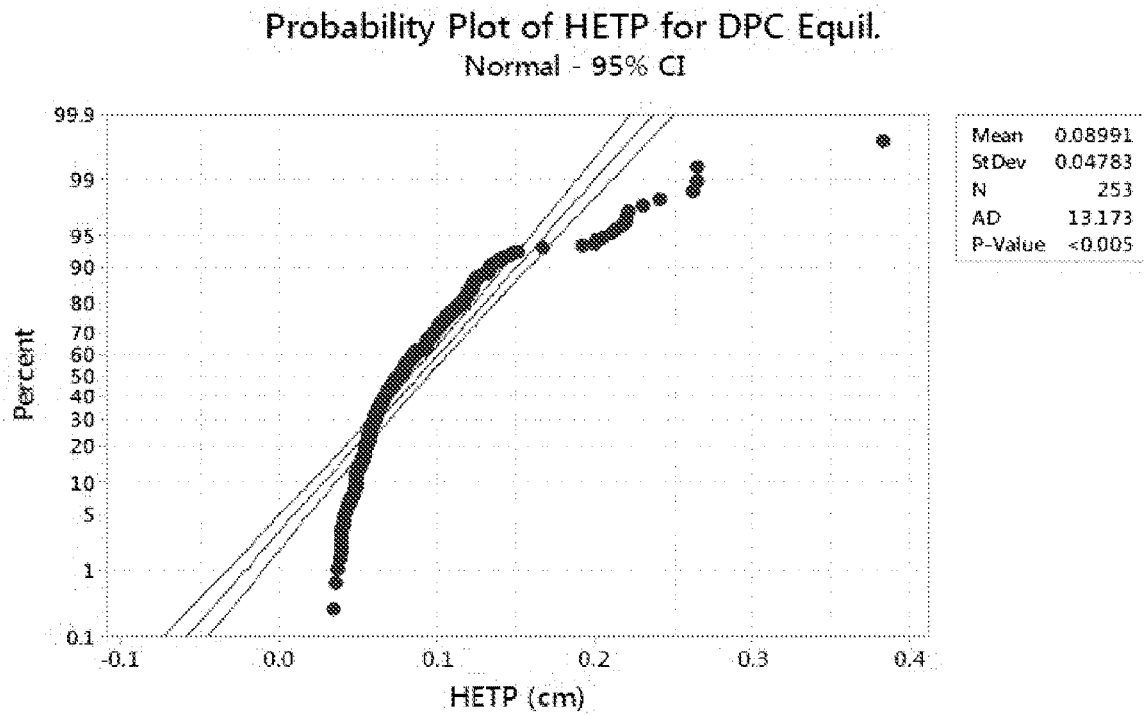
FIG. 3 is a probability plot of HETP for Protein A column equilibration front without transformation.
Figure 4:
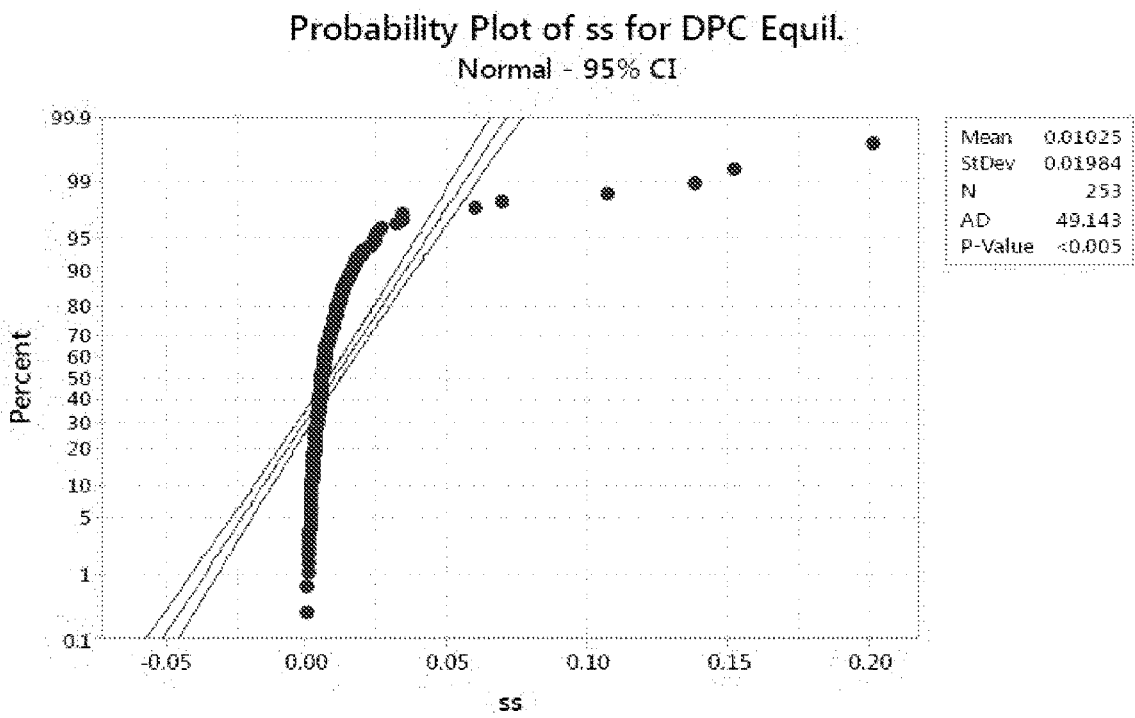
FIG. 4 is a probability plot of the sum of squares (SS) for Protein A column equilibration front without transformation.
Figure 5:
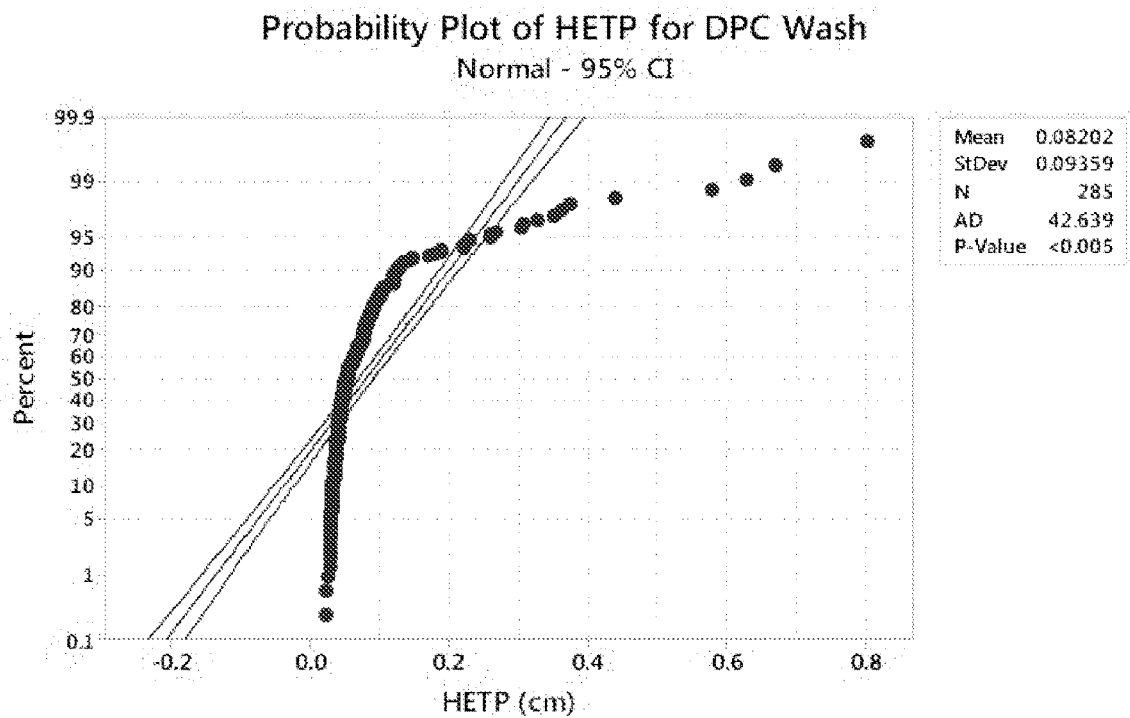
FIG. 5 is a probability plot of HETP for Protein A column wash front without transformation.
Figure 6:
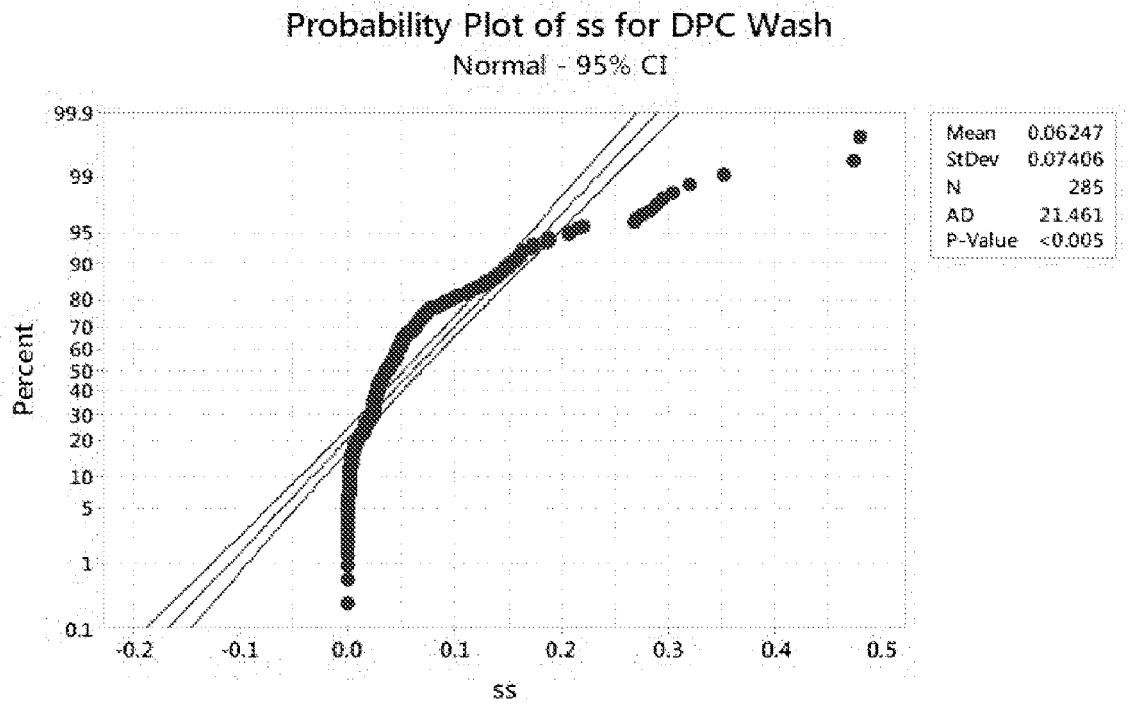
FIG. 6 is a probability plot of SS for Protein A column wash front without transformation.
Figure 7:
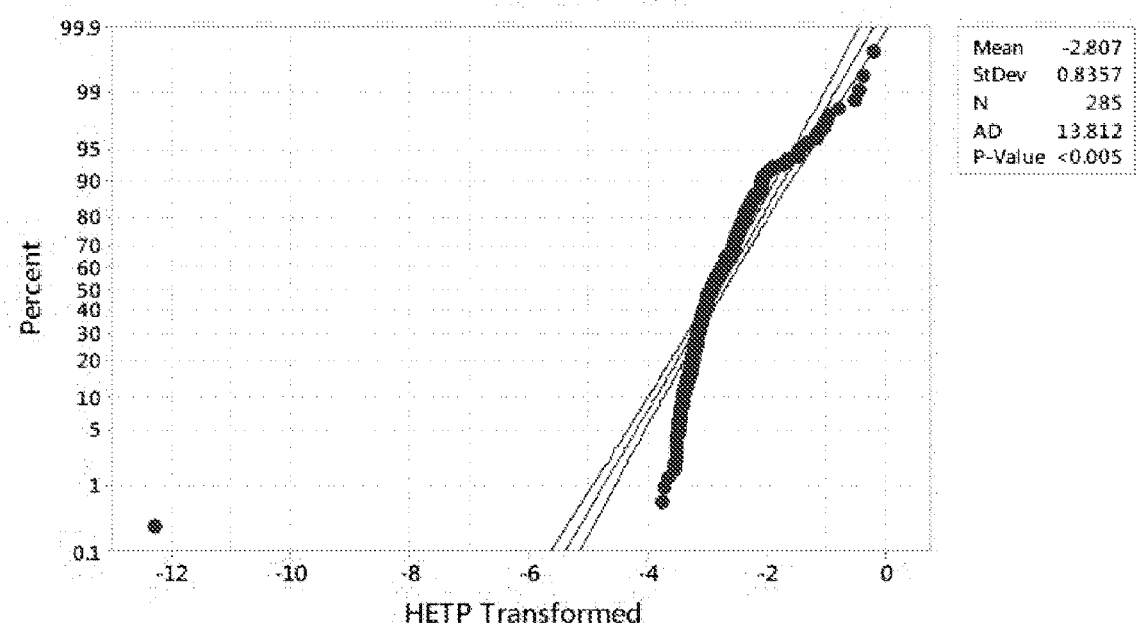
FIG. 7 is a probability plot of HETP for Protein A column equilibration front with natural log ($\lambda$=0) transformation.
Figure 8:
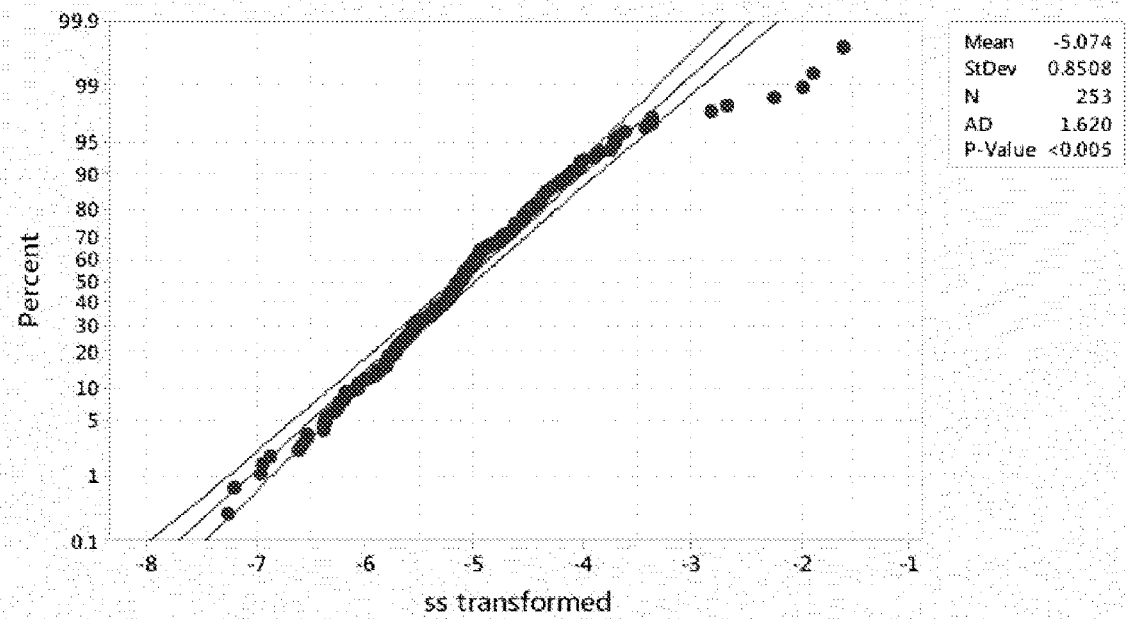
FIG. 8 is a probability plot of SS for Protein A column equilibration front with natural log ($\lambda$=0) transformation.
Figure 9:
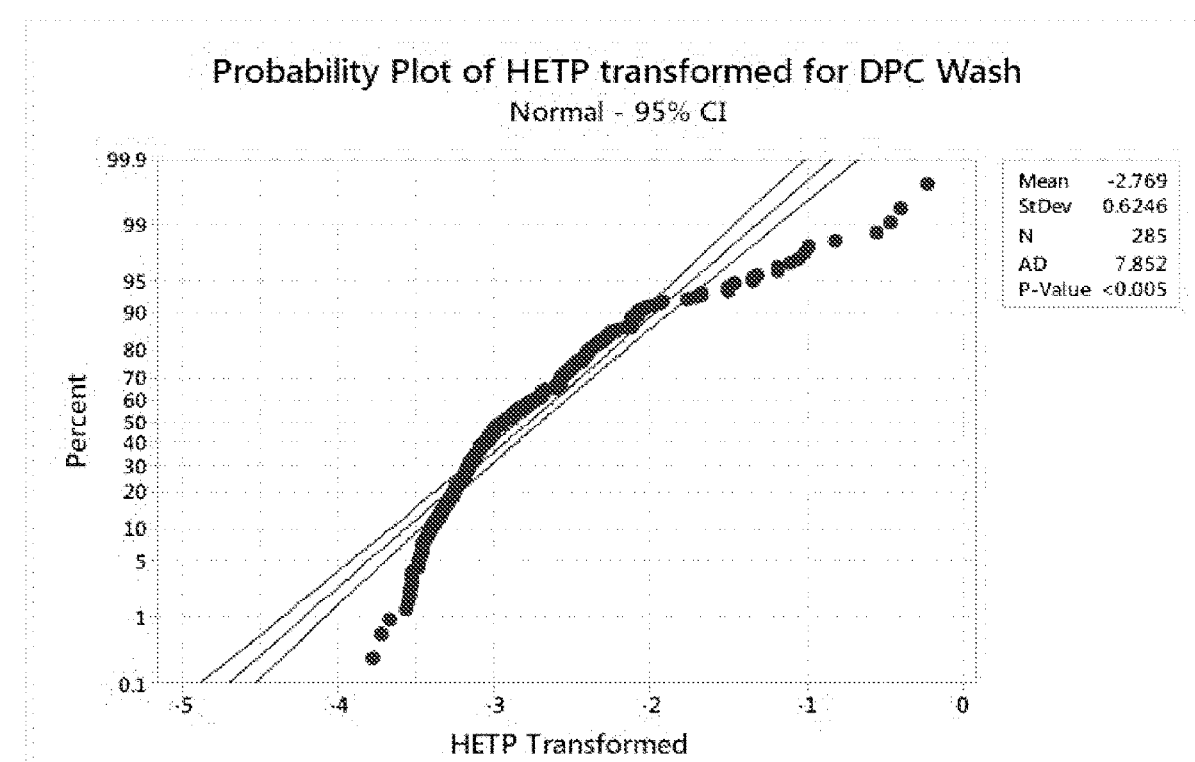
FIG. 9 is a probability plot of HETP for Protein A column wash front with natural log ($\lambda$=0) transformation.
Figure 10:
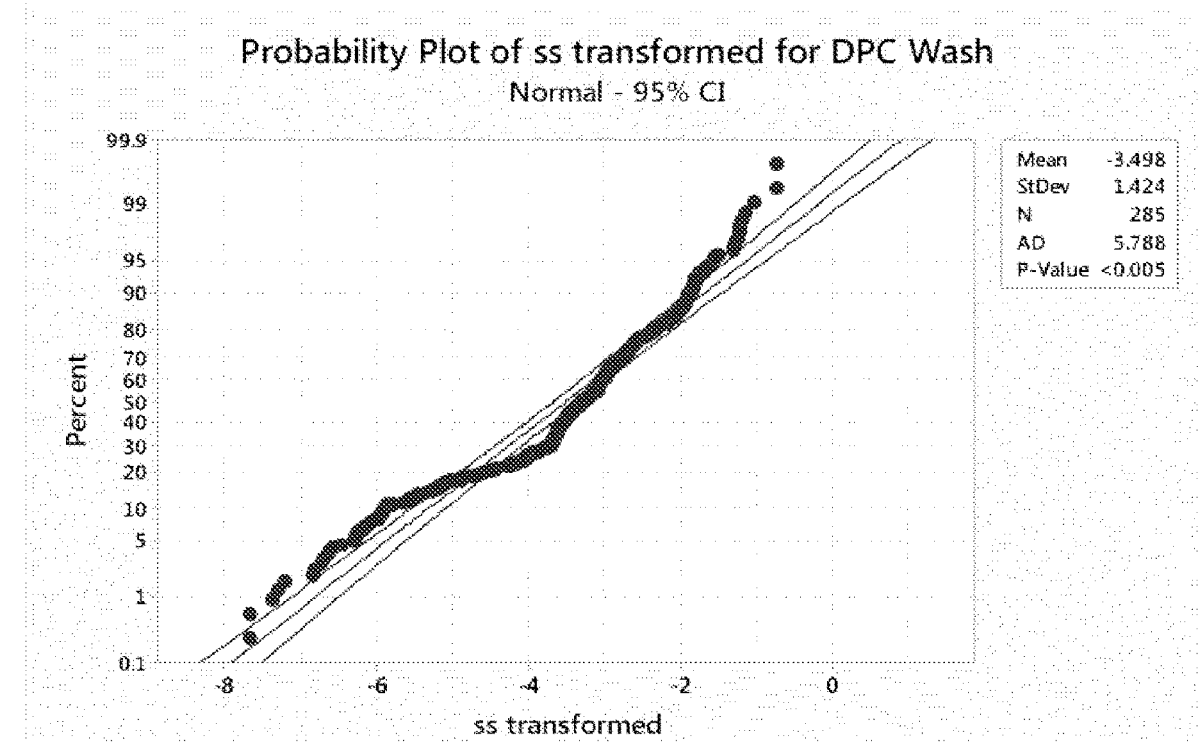
FIG. 10 is a probability plot of SS for Protein A column wash front with natural log ($\lambda$=0) transformation.

FIG. 2 is a diagram providing an overview of the method and system of operating a chromatography column and assessing column efficiency in real-time as described herein. As shown in FIG. 2 and described supra, the system 10 includes a chromatography column 12 used to separate biomolecules introduced into the column as a complex mixture, i.e., eluent 14, a detector 20 that detects a column output signal in the eluate as it elutes from the chromatography column, a communications interface 22 that transmits signal/data from the detector 20, a column qualification computing device 24, and a server 26.

Chromatography column 12 is filled with a permeable, semi-permeable, or impermeable solid phase column packing material. Suitable chromatography columns and column packing material are described supra. The eluent 14 containing the biomolecules of interest is introduced into the chromatography column 12. A mobile phase 16 is also introduced to the chromatography column 12. The mobile phase 16 facilitates separation of the biomolecules through the stationary phase of the chromatography column 12 and elution of the biomolecules in the eluate through the output 18 of the chromatography column. In accordance with the method as described herein, the mobile phase 16 comprises the sequentially introduced column buffers and/or wash reagents that differ in one or more physical or chemical properties from each other as described infra, e.g., pH, conductivity, salt concentration. These differences in one or more physical or chemical properties are detected in the eluate by the detector 20.

Detector 20 is coupled to the output 18 of chromatography column 12. Accordingly, detector 20 monitors and collects the column output signal via the eluate of chromatography column 12. Suitable detectors and the properties of the eluate, i.e., the column output signal, detected are described supra. The detector is coupled to a communications interface unit 22 that transmits data collected by the detector 20 (e.g., column output signal and accumulated flow parameters) to a column qualification computing device 24 for data processing and/or a server 26 for storage.

The column qualification computing device 24 of the system described herein can be any computing device, e.g., a computer, a personal computing device, smartphone, etc. that includes a central processing unit (CPU) or processor 32, a memory 30, a network interface 28, and a user interface 34 which are coupled together by a bus 36 or other link. The column qualification computing device 24 may include other types and/or numbers of components and elements in other configurations.

The processor 32 in the column qualification computing device 24 executes a program of stored instructions for one or more aspects of gamma distribution transition analysis described and illustrated by way of the examples herein, although other types and/or numbers of processing devices could be used and the processor 32 can execute other types and/or numbers of programmed instructions. In one embodiment, the processor 32 is located solely on the column qualification computing device 24. In another embodiment, the processor is distributed between the detector 20 and the column qualification computing device 24. For example, in one embodiment, the processor 32 of the column qualification computing device 24 comprises a microcontroller that is coupled to the detector. In this embodiment, the microcontroller serves as an on-board processor that is capable of mapping or converting data collected by the detector 20 into a digital signal that is transmitted to the column qualification computing device 24. The microcontroller coupled to the one or more detectors is capable of carrying out one or more processing functions of the column qualification computing device 24.

The memory 30 in the column qualification computing device 24 stores these programmed instructions for one or more aspects of the GDTA as described herein. A variety of different types of memory storage devices, such as a random access memory (RAM) and/or read only memory (ROM) in the timing processor device or a floppy disk, hard disk, CD ROM, DVD ROM, or other computer readable medium which is read from and written to by a magnetic, optical, or other reading and writing system that is coupled to the processor 32 in the column qualification computing device 24, can be used for the memory 30.

The network interface 28 of the column qualification computing device 24 operatively couples and facilitates communication between the column qualification computing device 24 and the detector 20, although other types and/or numbers of communication networks or systems with other types and/or numbers of connections and configurations can be used.

The column qualification computing device 24 may further comprise a user interface 34, such as, for example, a graphical user interface, a touch user interface, or a web-based user interface. The user interface is configured to display information regarding the chromatography column qualification parameters to the user. The user interface is also configured to receive input from the user regarding the chromatography column parameters.

The server 26 depicted in FIG. 2 can be one or a plurality of computing devices that each include a CPU or processor, a memory, and a network interface, which are coupled together by a bus or other link similar to that described for the column qualification computing device 24. The server 26 may include other types and/or numbers of components and elements in other configurations.

Communication interface(s) 22 of the system described herein can include one or more local area networks (LANs) and/or wide area networks (WANs). By way of example only, the communication interface(s) 22 can use TCP/IP over Ethernet and industry standard protocols, including hypertext transfer protocol (HTTP) and/or secure HTTP (HTTPS), although other types and/or numbers of communication networks may be utilized.

Another aspect of the present disclosure relates to a non-transitory computer readable medium having stored thereon instructions for chromatography column qualification using the gamma distribution transition analysis. These instructions comprise executable code which when executed by a processor, causes the processor to perform steps comprising, collecting column outlet signal and accumulated flow parameters at two or more intervals of at least one mobile phase transition front during a first operation of the chromatography column comprising column packing; determining a model gamma cumulative distribution curve based on the collected column outlet signal and accumulated flow parameters for the at least one mobile phase transition front using Formula Ia as described supra for a rising transition front or Formula Ib as described supra for a falling transition front; calculating a height equivalent theoretical plate (HETP) value for the at least one mobile phase transition front using Formula II as described supra and the model gamma cumulative distribution curve parameters of k, θ, and $V_i$ as described herein; and assessing quality of the chromatography column packing based on said calculated HETP value.

Another aspect of the present disclosure is directed to a chromatography column qualification device. This device comprises a processor and a memory coupled to the processor. The memory is configured to execute programmed instructions stored in the memory. These instruction include: collect column outlet signal and accumulated flow parameters at two or more intervals of at least one mobile phase transition front during a first operation of the chromatography column comprising column packing; determine a model gamma cumulative distribution curve based on the collected column outlet signal and accumulated flow parameters for the at least one mobile phase transition front using Formula Ia for a rising transition front or Formula Ib for a falling transition front as described supra; calculate a height equivalent theoretical plate (HETP) value for the at least one mobile phase transition front using Formula II as described supra and the model gamma cumulative distribution curve parameters of k, θ, and $V_i$ as described herein, and assess quality of the chromatography column packing based on said calculated HETP value.

EXAMPLES

Example 1—Application of the Gamma Distribution Transition Analysis for Column Qualification of Protein a Chromatography Columns Used in to REMICADE® (Infliximab) Manufacturing Overview:

The manufacturing process of the therapeutic antibody, REMICADE® (infliximab), involves several stages, four of which involve chromatography purification. The gamma distribution transition analysis (GDTA) for column qualification was applied to two or three transitions during each of these column steps. This Example describes the application of the GDTA method to the Protein A column purification step employed during REMICADE® (infliximab) manufacturing. The purification process includes two transition fronts, i.e., equilibration and intermediate wash, that are appropriate for GDTA as described herein.

The GDTA was executed on 129 fronts from the consecutive purification of 69 batches of REMICADE® (infliximab), comprising 60 equilibration and 69 wash fronts. The gamma front distribution analysis was performed concurrently with manufacturing and did not impact the manufacturing process. All manufacturing, monitoring and controls were performed using current, effective procedures. During the column chromatography purification of REMICADE® (infliximab), conductivity (i.e., the column outlet signal) and flow of the eluent (i.e., accumulated flow) were recorded.

In addition to the application of the GDTA to column operation in real time, historical data for 285 batches processed over the course of the four previous years was also collected and analyzed as described herein. The data set included 253 equilibration fronts and 285 wash fronts, for a total of 538 historical fronts. The equilibration fronts were not generated for 32 batches in which pre-use sanitizations were performed. This data set was selected to provide an even distribution through the life of the columns and represents 11 column packs.

GDTA Protocol:

For each transition front during Protein A column purification, i.e., wash and equilibration, the conductivity and accumulated flow were recorded. Determination of the starting point was accomplished by evaluating the trends for pre-column conductivity and pressure in order to identify the point at which the column was placed inline. A spreadsheet was created and setup to retrieve flow and conductivity data from the server using a calculated 10 second interval for the duration of the front.

The conductivity data was normalized by setting the maximum value to 1 and the minimum value to 0 and scaling the other points proportionally. Additionally, the flow was converted to column volumes.

A starting gamma CDF was calculated by using the same starting k, θ, $V_i$ parameters as the PI module. $V_i$ was subtracted from each volume value in the x term of the gamma distribution function. In order to normalize the conductivity, which was increasing during the purification, the conductivity values were set to 0 for volumes less than $V_i$ and the maximum was set to 1.

The difference (error) between each conductivity value and the model fit for each volume point was calculated. Additionally, the sum of squares for the error between 0.5 and 1.8 CV was calculated. The best fit gamma CDF parameters were calculated using the Excel solver to find the k, θ, and $V_i$ parameters that produced a model curve with the minimum value for the sum of squares using $$C = 1 - \frac{1}{\Gamma(k)} \gamma\left(k, \frac{V - V_i}{\theta}\right). \quad \text{Formula Ia}$$

The solver was run for 10,000 iterations using the GRG non-linear method with constraints of k≥0.0001 and $V_i$≥0 to ensure that a closest fit was reached.

The following parameters were calculated from the final values of k, θ, and $V_i$:

Mean $(V_m)$, $\mu = k\theta + V_i$,

Variance, $\sigma^2$ (sigma squared) $= k\theta^2$

Mode $= (k-1)\theta + V_i$ $$HETP = \frac{L}{N_p} = \frac{\sigma^2}{\mu^2} L = \frac{k\theta^2 L}{(k\theta + V_i)}$$

The average flow rate and pre-column pressure was calculated for the period from 0.5 to 1.8 CV for each front.

Analysis and Evaluation of Acceptance Criteria:

Normality

Results for HETP and SS for both the equilibration and wash fronts were evaluated for normality by creating a probability plot. In the probability plots (FIGS. 3-12) the data points (results for HETP or SS) represent the actual cumulative distribution observed in the sample. The lines represent the fitted cumulative distribution and the upper and lower confidence intervals based on a normal distribution using the parameters estimated from the sample. The percentile scale is transformed so the fitted distribution forms a straight line. The HETP and SS data sets are each bounded by 0 on the lower end, however, the normal distribution model suggests negative values. The resulting probability plots show a curved shape. See FIGS. 3-6. Thus, the results fit better using a log transformation. See FIGS. 7-10 for the probability plot of the log transformed data.

Figure 11:
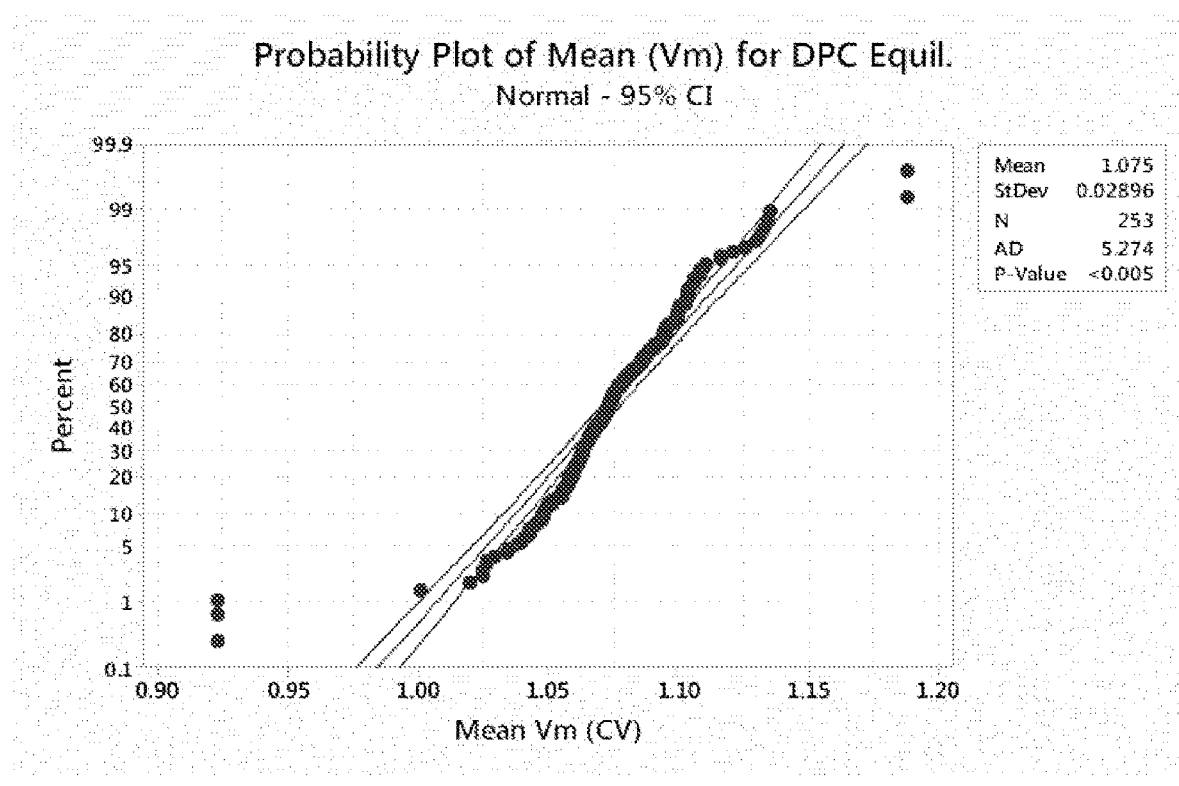
FIG. 11 is a probability plot of the Mean ($V_m$) for Protein A column equilibration.
Figure 12:
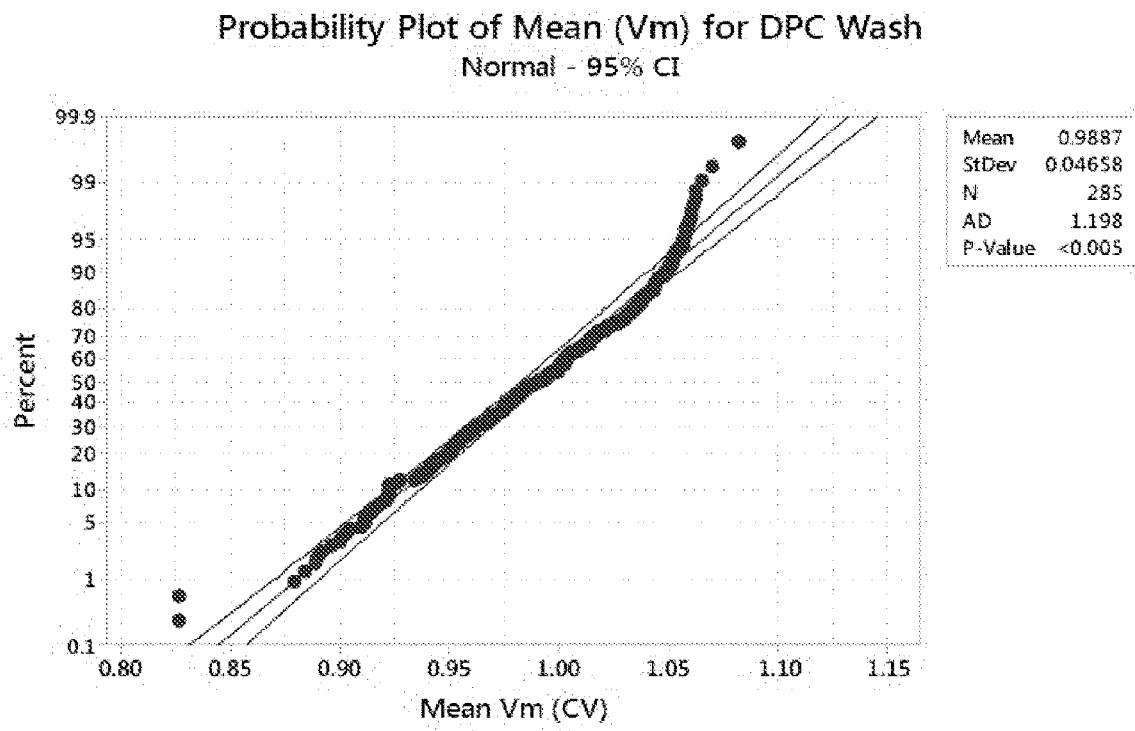
FIG. 12 is a probability plot of the Mean ($V_m$) for Protein A column wash front.

Data for the Mean $(V_m)$ was also evaluated for normality. FIG. 11 and FIG. 12 show that the data fits the normal distribution, with only a few outliers. Thus, no transformation was needed. This parameter was not specified in the protocol but provides a useful assurance that the curve fit is valid. Control limits for this parameter will also be generated from this analysis.

Identification of Outliers and Causes of Variation.

In order to identify outliers and assess variability in the results, control charts for each parameter were generated. See FIGS. 13-22. Control charts used the transformed data for the HETP and SS, where natural log transformation was applied. The data is also plotted in a time series plot with the transformed upper control limit for each of these parameters.

Figure 13:
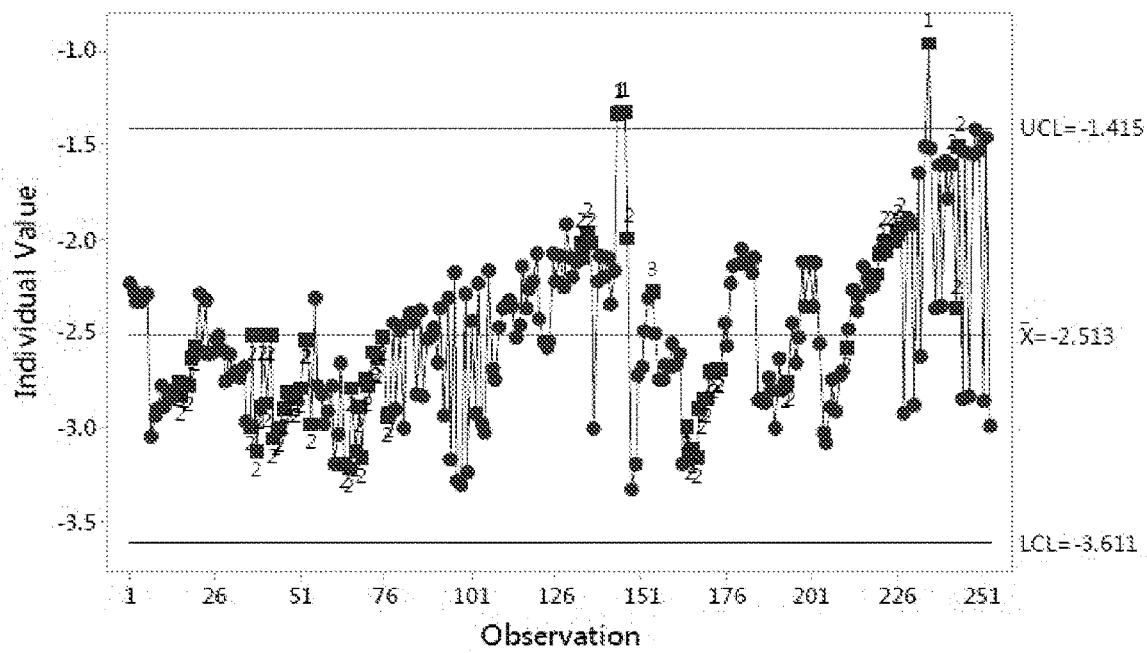
FIG. 13 is a control chart of HETP for Protein A column equilibration front with natural log ($\lambda$=0) transformation. UCL=upper control limit; LCL=lower control limit. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 18:
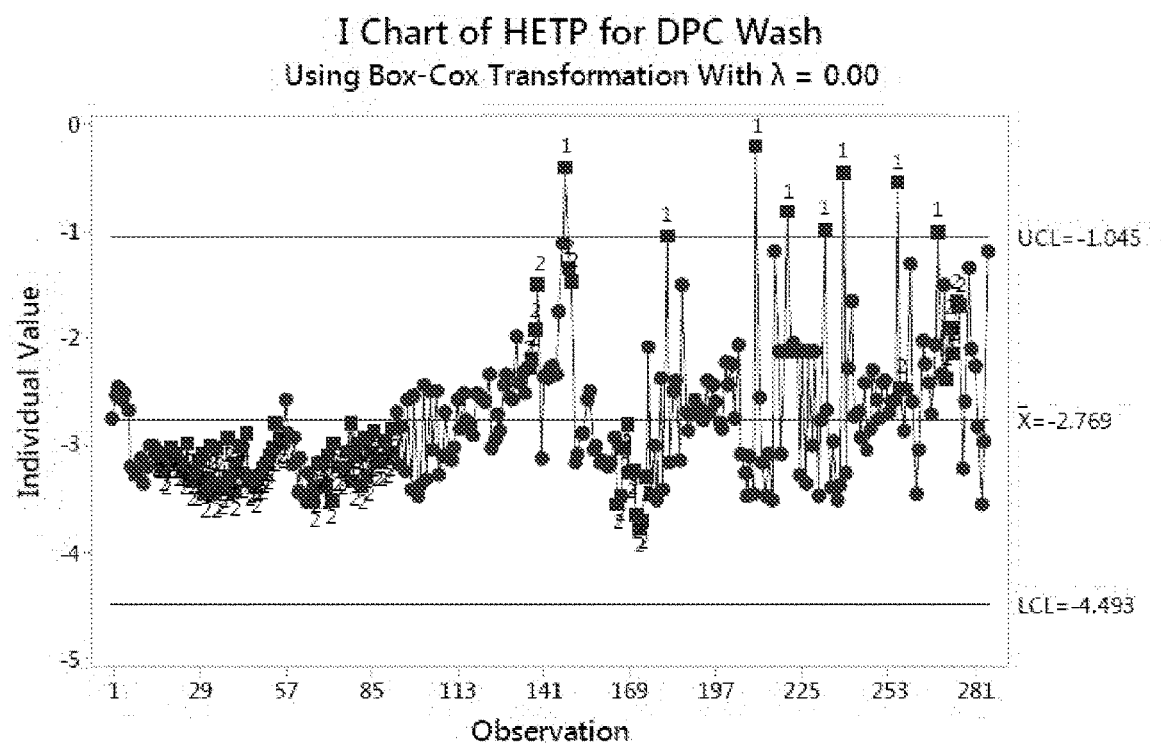
FIG. 18 is a control chart of HETP for Protein A column wash front with natural log ($\lambda$=0) transformation. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

HETP:

A number of outliers and trends are apparent in the HETP results for both Equilibration and Wash fronts. Additionally, FIG. 13 and FIG. 18 show trends in the data based on Shewhart rules 1, 2 and 3, represented by squares in the figures and numbered according to the following.

Test Rule 1 1 point is outside the control limits.

2 8 points on the same side of the center line.

3 6 consecutive points are steadily increasing or decreasing.

The batches associated with these excursions were not excluded from the analysis as they are representative of the acceptable process.

Both of the control charts (FIG. 13 and FIG. 18) show a number of Shewhart rule 1 violations, which also exceeds the control limits. In each case the issues were identified and corrected by reconditioning the columns.

Figure 23:
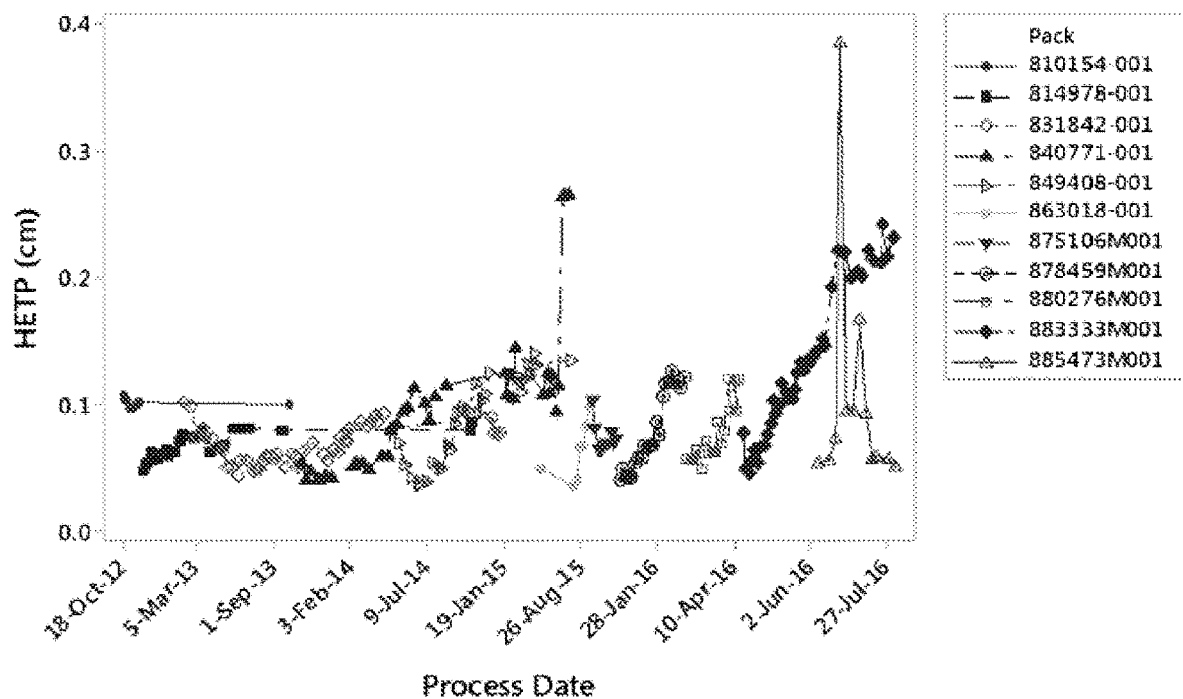
FIG. 23 is a time series plot of HETP results for direct product capture (DPC) Protein A column equilibration front grouped by column pack.
Figure 24:
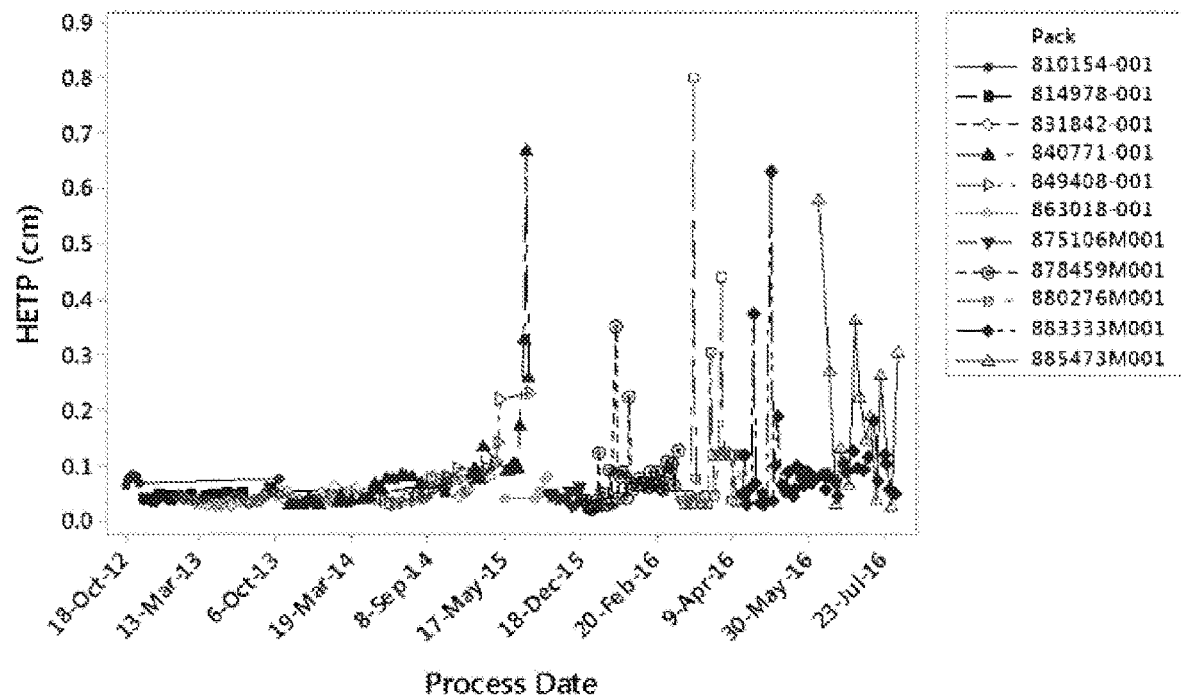
FIG. 24 is a time series plot of HETP results for DPC Protein A column wash front grouped by column pack.
Figure 25:
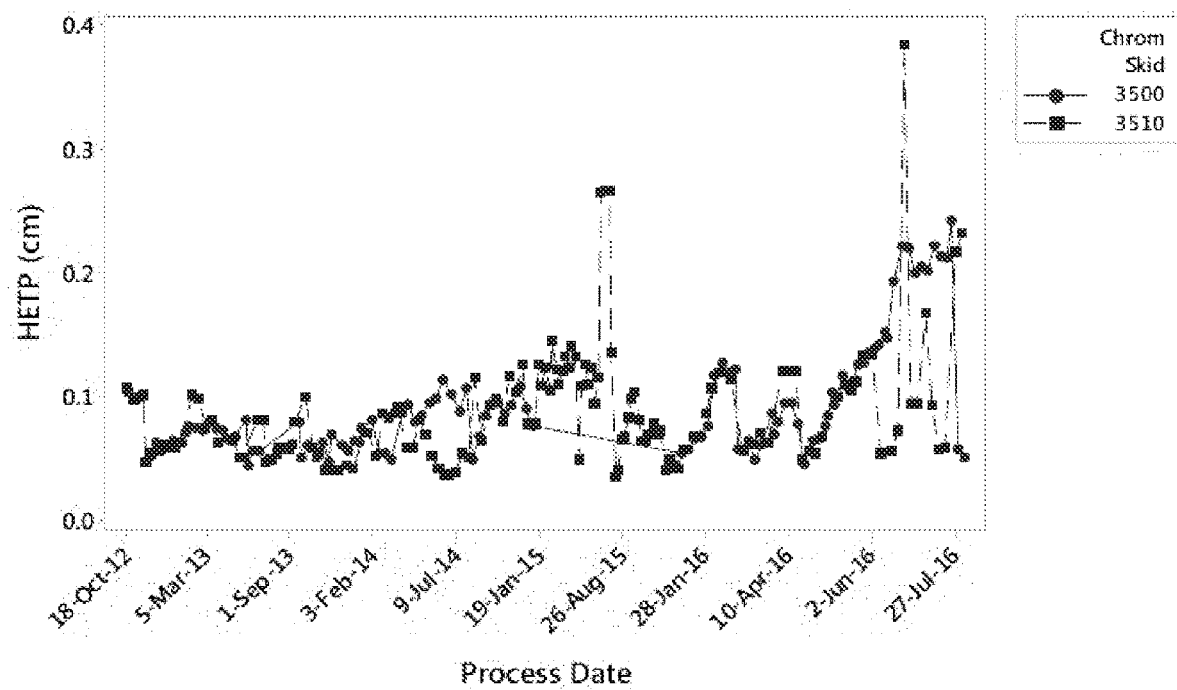
FIG. 25 is a time series plot of HETP results for DPC Protein A column equilibration front grouped by skid.
Figure 26:
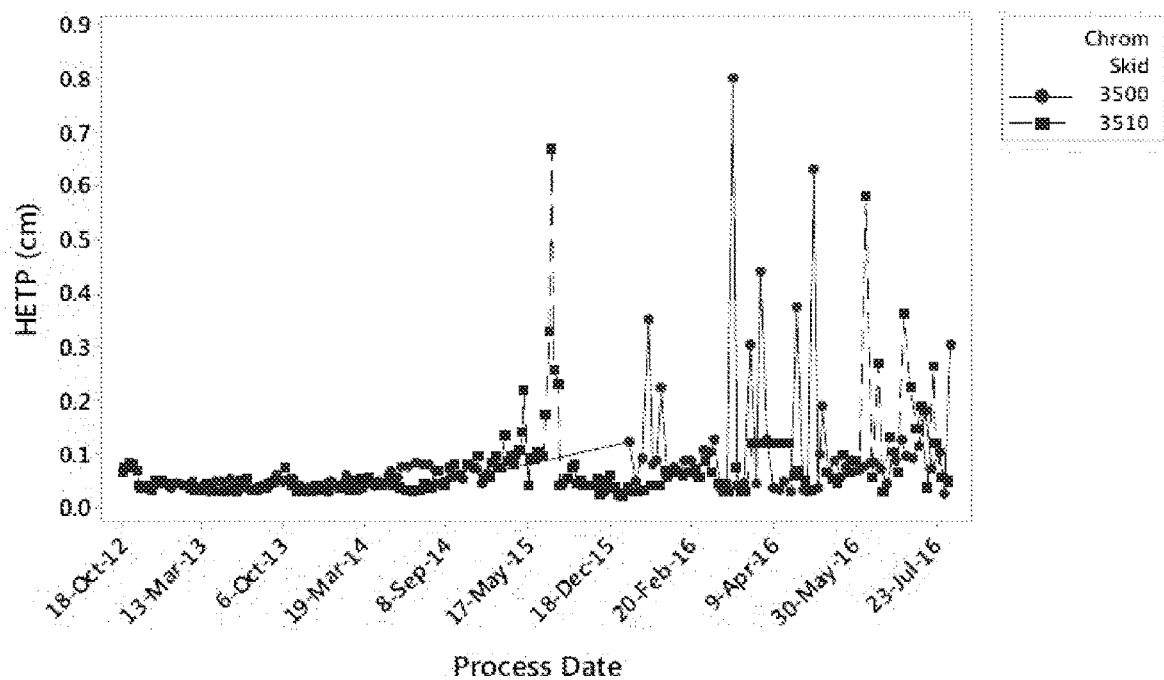
FIG. 26 is a time series plot of HETP results for DPC Protein A column wash front grouped by skid.
Figure 27:
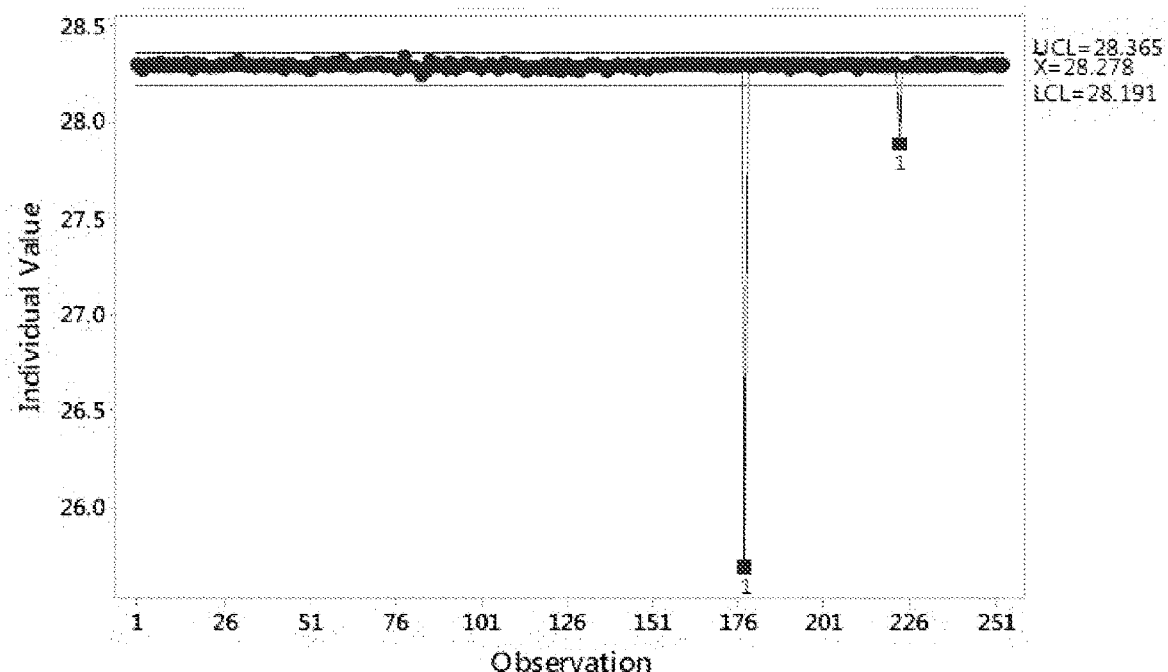
FIG. 27 is chart showing the average flow for DPC Protein A column equilibration. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 28:
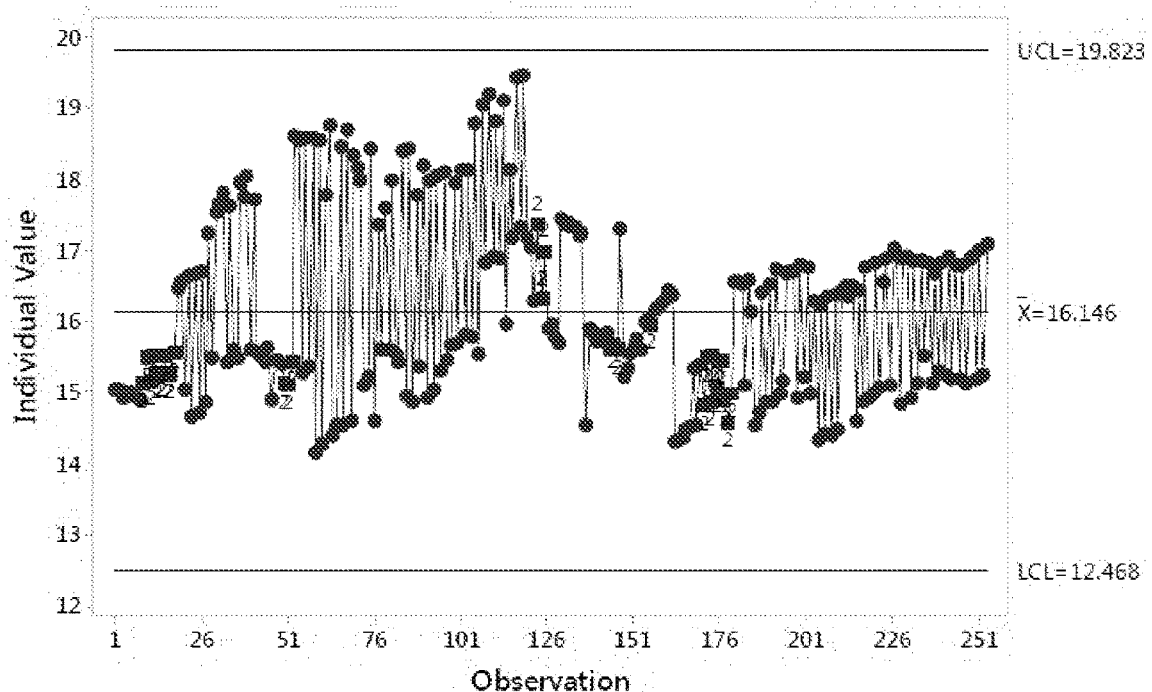
FIG. 28 is a chart of the average pre-column pressure during equilibration. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 29:
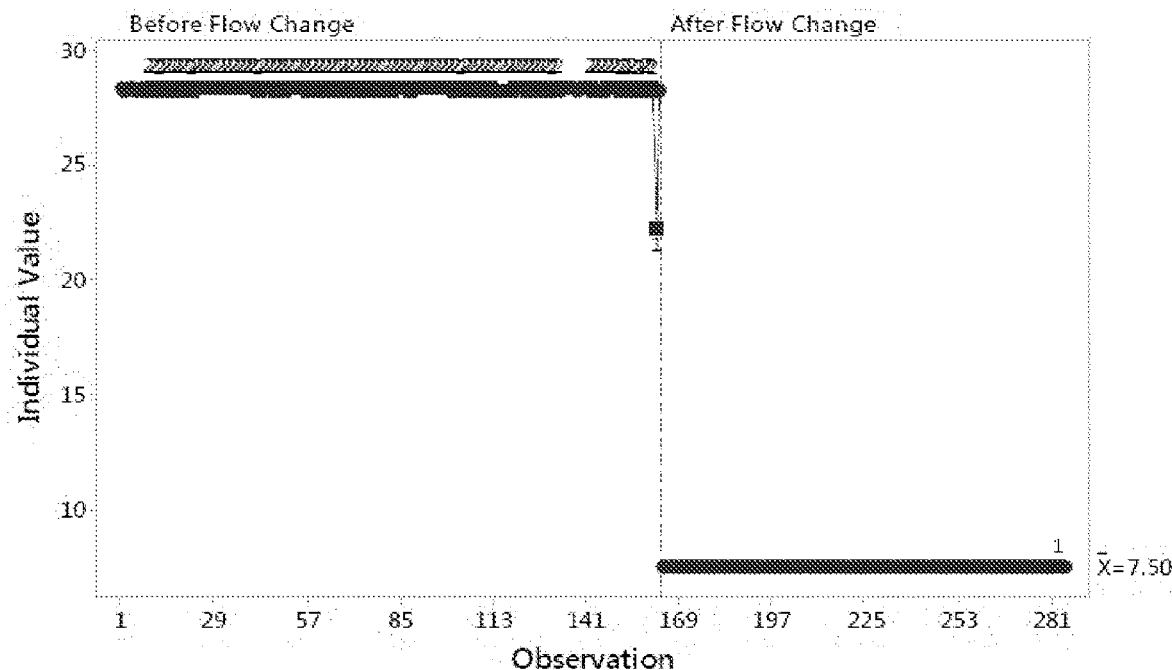
FIG. 29 is a chart of the average wash flow rate for DPC Protein A column wash front. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 30:
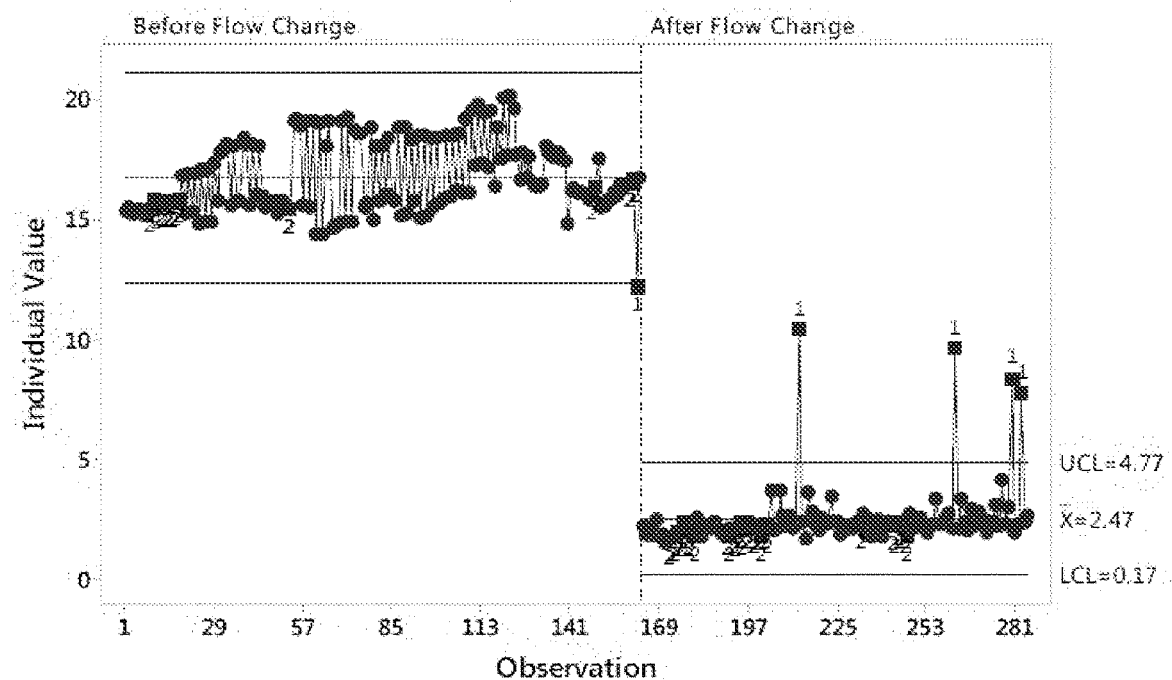
FIG. 30 is a chart of the average wash pressure for the DPC Protein A column wash front. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

As expected, a number of runs met the criteria for rule 2 and 3 due to variation in the column packs. In order to further assess the trends, time series plots were prepared with data grouped by column pack (FIGS. 23-24) and skid (FIGS. 25-26). These charts show that much of the special cause variation is attributed to column degradation and some isolated excursions. Trends of increasing HETP are apparent for each column over time for the equilibration front (FIG. 23). Excursions observed for the Wash front appear to be isolated to one skid or the other at different times (FIG. 26), suggesting that there may be a source of column performance variability in the skid.

Figure 15:
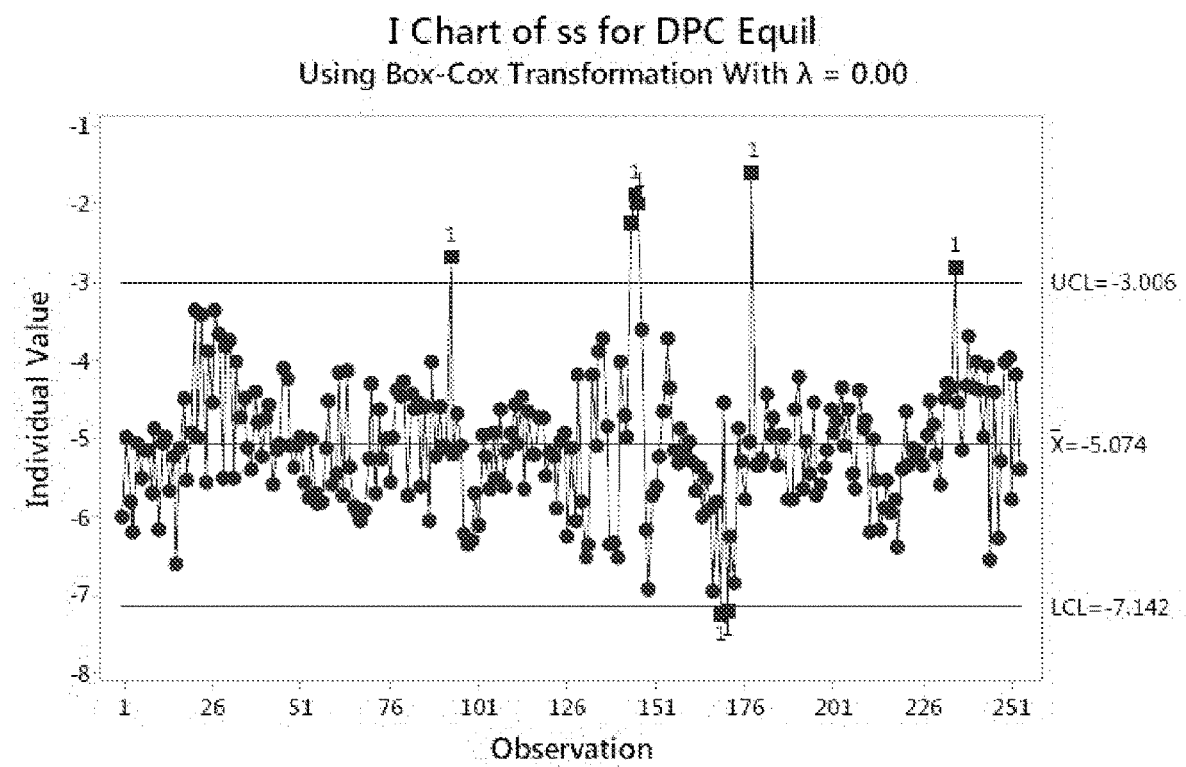
FIG. 15 is a control chart of the SS for Protein A column equilibration front with natural log ($\lambda$=0) transformation. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 20:
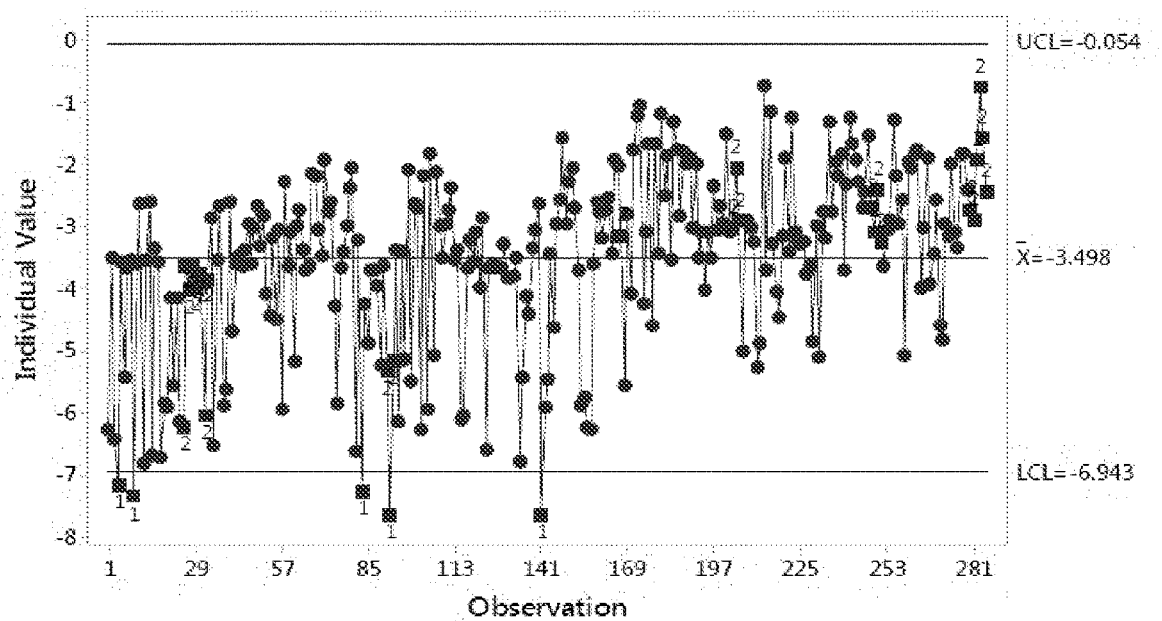
FIG. 20 is a control chart for SS for Protein A column wash front with natural log ($\lambda$=0) transformation. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 21:
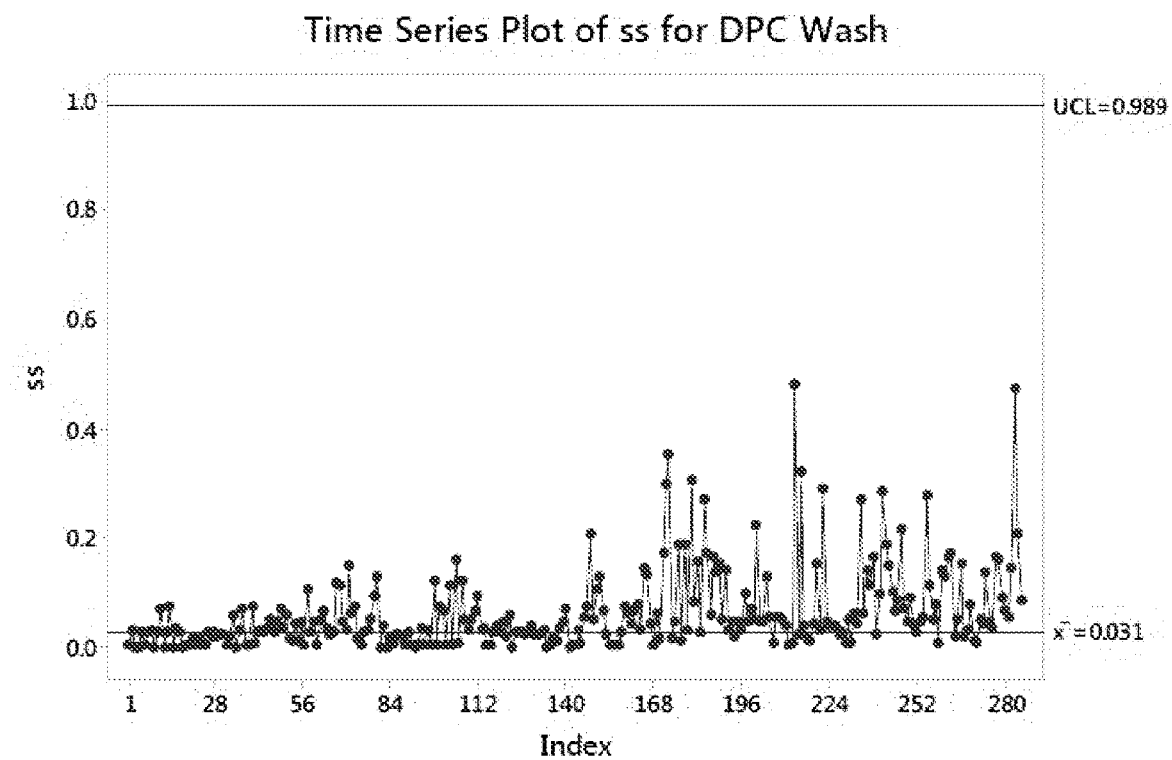
FIG. 21 is a time series plot of SS for Protein A column wash front. UCL is derived from transformed data in FIG. 20.
Figure 22:
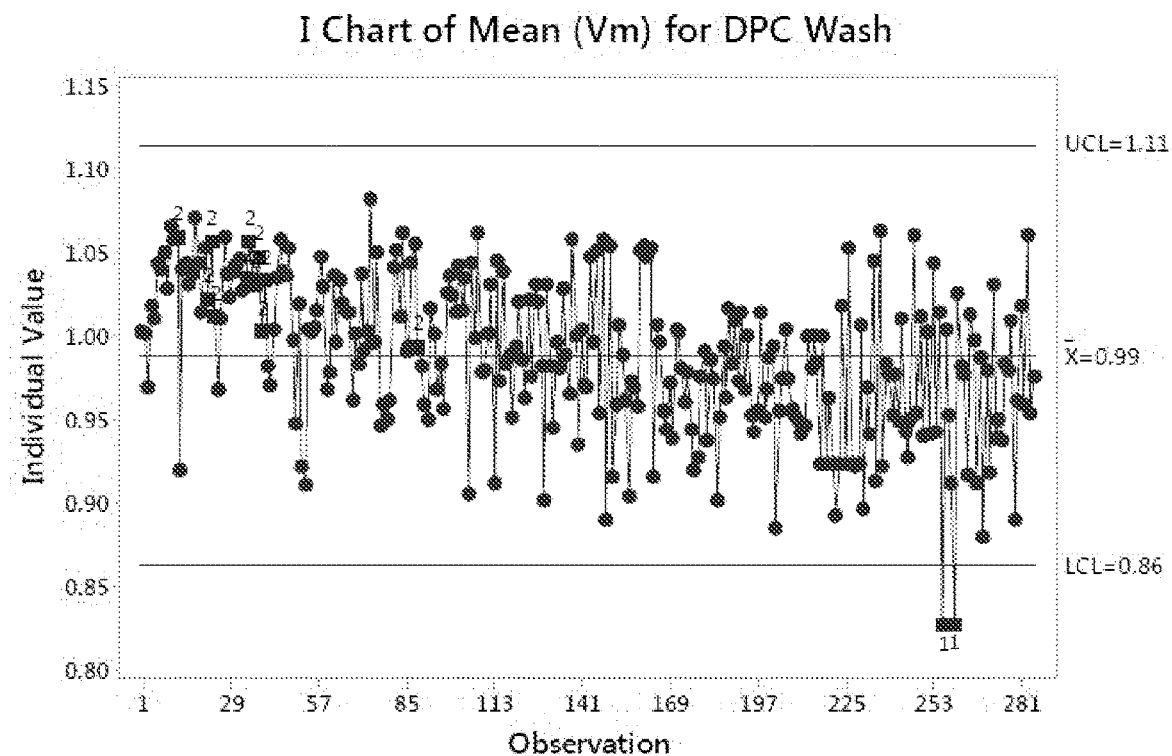
FIG. 22 is a control chart for Mean ($V_m$) for Protein A column wash front. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

Sum of Squares (SS):

The sum of squares is a measure of how well the gamma distribution fits the process data. This measure will provide a check to ensure that the HETP result is valid. Control charts for the transformed data are shown in FIG. 15 and FIG. 20 for equilibration and wash, respectively. This measure only has an upper control limit. FIG. 15 shows 6 points where the upper control limit is exceeded. Four of these are associated with higher HETP. Batch 880572M had a flow disruption during the front which caused the SS to be high but did not impact HETP.

Evaluation of Flow and Pressure.

The average flow rate and pre-column pressure for the data set was evaluated to identify any outliers. The relationship between the differences identified and the results was assessed.

Figure 31:
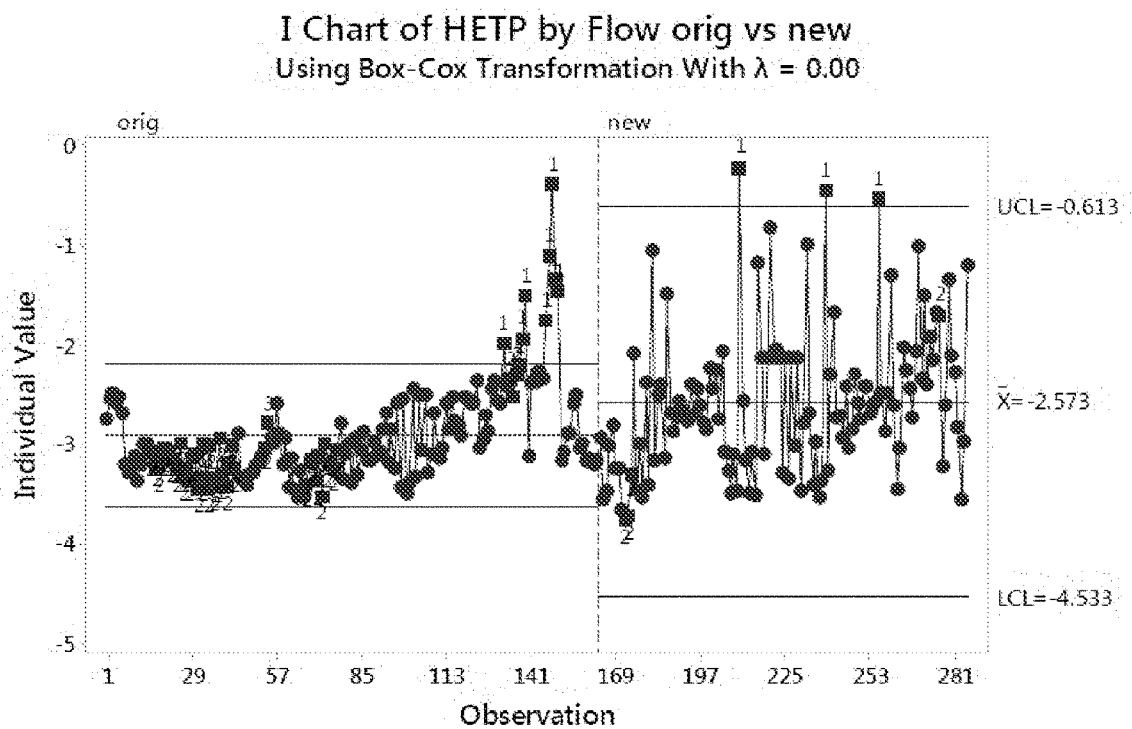
FIG. 31 is a chart showing the HETP before and after changing the wash flow rate. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

Flow rate and pre-column pressure are trended in FIGS. 27-30. The charts show excellent control of flow rate for each of the steps. The Wash flow rate was changed during this assessment. Pre-Column pressure shows variations related to the skid and columns but is generally stable within a range. FIG. 31 shows that the HETP value is not significantly impacted by the wash flow rate change.

Control limits for Protein A Column

HETP:

HETP is directly related to the column performance and is also affected by other factors in the system that may increase dispersion. The result must be >0. The control limits for HETP are best determined by using the natural log Box-Cox transformation (λ=0), as shown in FIG. 13 for the equilibration and FIG. 18 for the wash front. The control charts show control limits for the transformed data calculated by Minitab using the mean+/−3 standard deviations (see also Table 2 below). Standard deviation is determined based on the average moving range. A moving range of 100 was selected to account for the variation in column performance over the column life. The upper and lower control limits are reverse transformed ($e^x$) to determine the control limits for the untransformed data.

Figure 14:
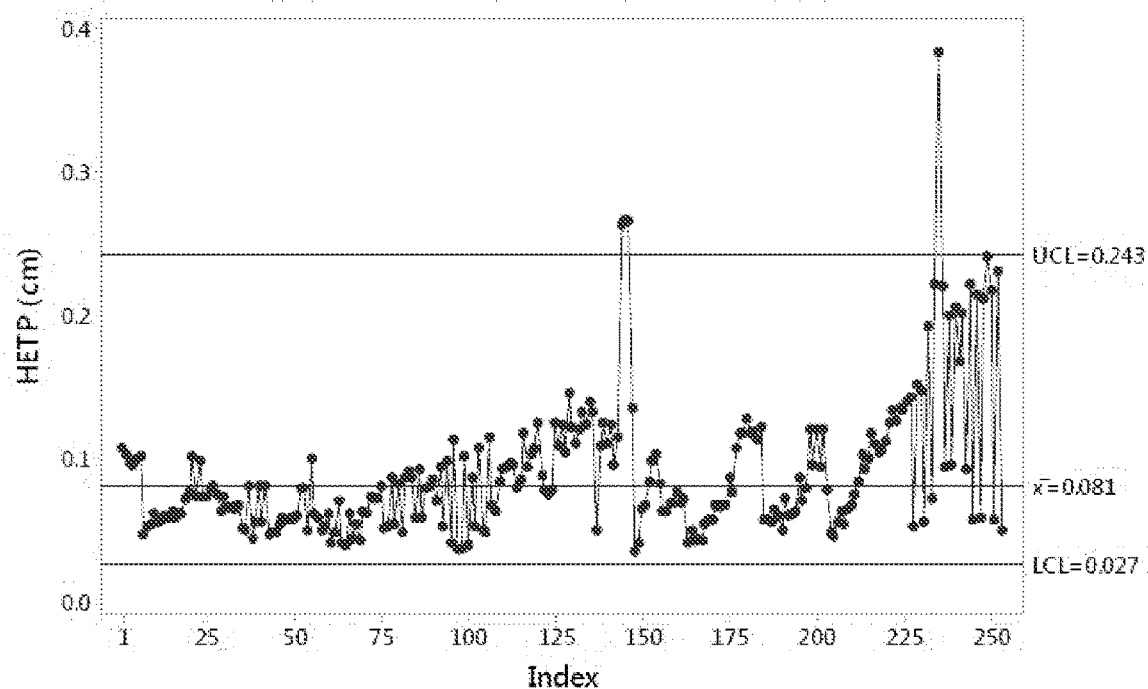
FIG. 14 is a time series plot of HETP for Protein A column equilibration front. The UCL is derived from transformed data in FIG. 13.
Figure 19:
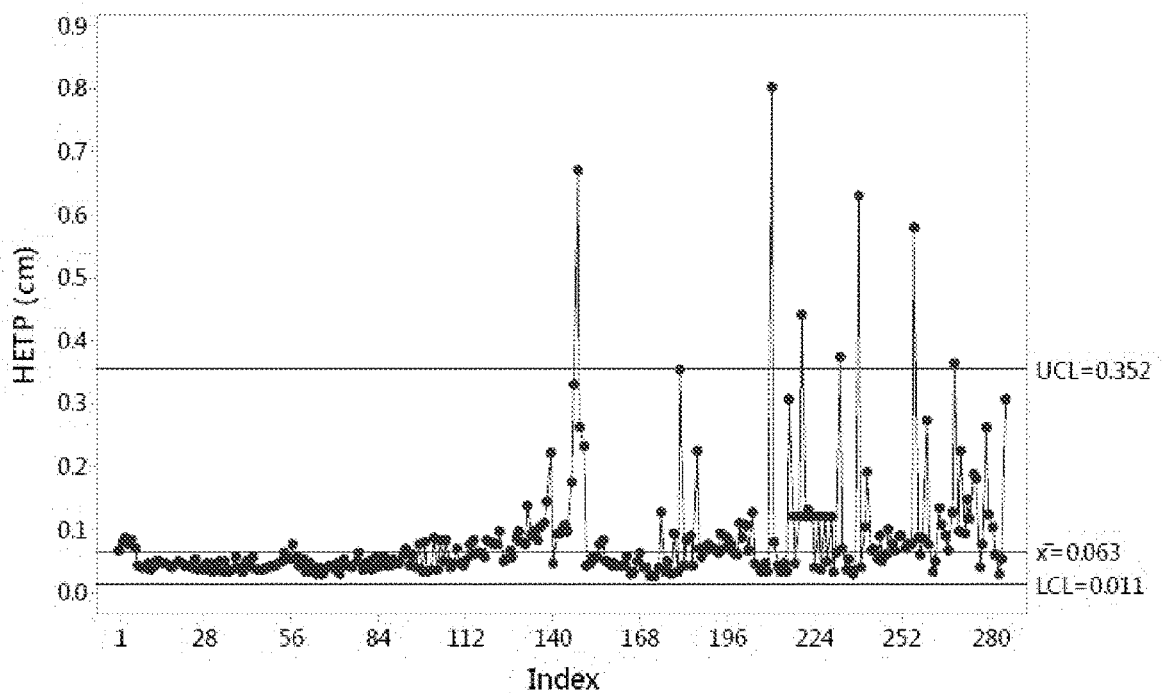
FIG. 19 is a time series plot of HETP for Protein A column wash front. UCL is derived from transformed data in FIG. 18.

A time series plot for each front's HETP results and control limits is shown in FIG. 14 and FIG. 19. Operation within these limits is expected to produce acceptable chromatographic performance based on this historical review. Values above the upper control limits may indicate column flow issues and should be evaluated further. Values below the lower control limits may be indicative of a calculation error.

Figure 16:
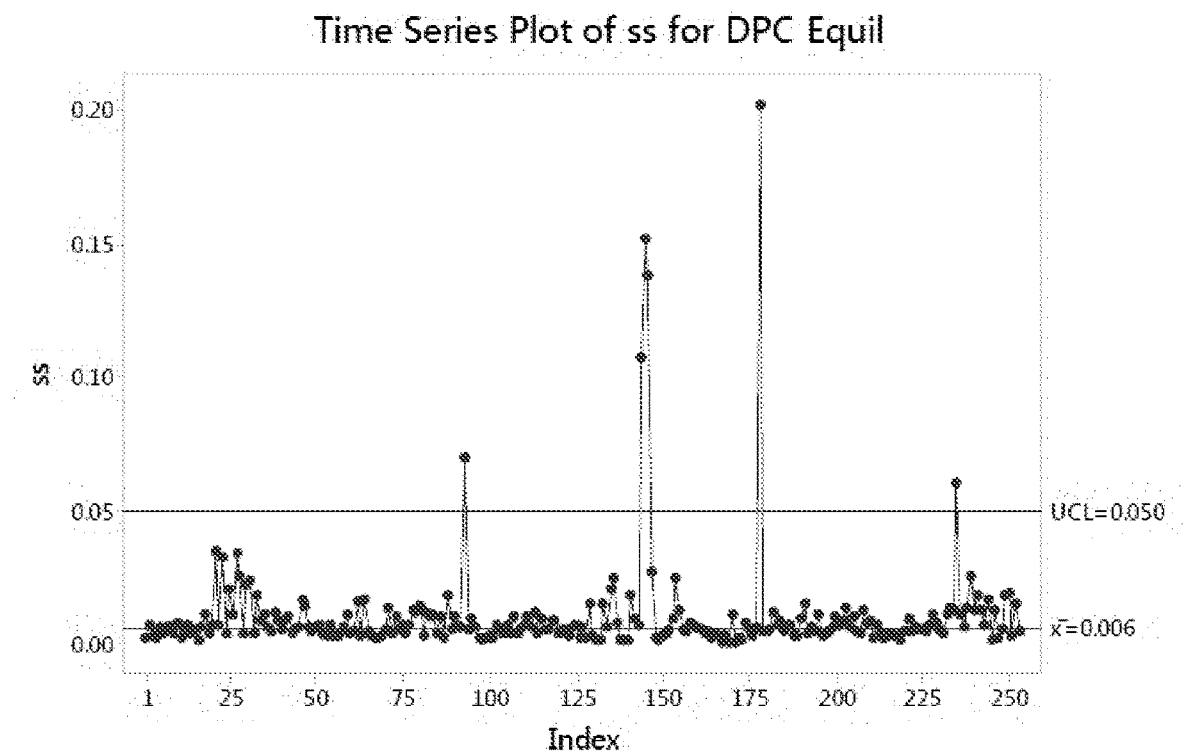
FIG. 16 is a time series plot of SS for Protein A column equilibration front. The UCL is derived from transformed data in FIG. 15.
Figure 17:
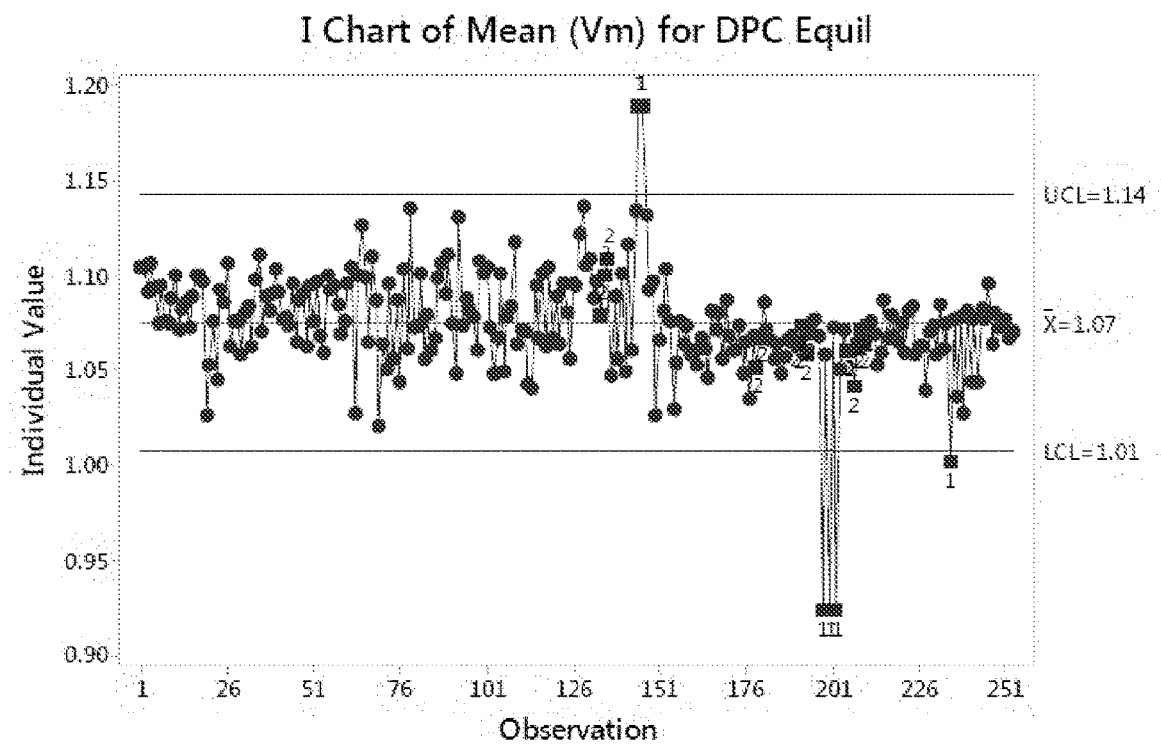
FIG. 17 is a control chart of the Mean ($V_m$) for Protein A column equilibration front. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

Sum of Squares (SS):

The SS is a measure of how well the gamma distribution model fits the data. This measure is used to ensure that HETP values calculated using the GDTA method represent the process data. There is no lower limit and the result must be >0. The upper control limit for SS is best determined by using the natural log Box-Cox transformation ($\lambda=0$), as shown in FIG. 15 for the equilibration front and FIG. 20 for the wash front. The control charts show control limits for the transformed data calculated by Minitab using the mean+/−3 standard deviations. Standard deviation is determined based on the average moving range. A moving range of 100 was selected to account for the variation in column performance over the column life. The control charts show upper control limits for the transformed data which are reverse transformed to give 0.050 and 0.989 for the Equilibration and Wash fronts, respectively (see Table 2). A time series plot for each front's SS results and control limits is shown in FIG. 16 and FIG. 20. Results within the limits will ensure that the model fits the data as well as historical results. If the result is outside of this range, a special cause is likely.

Mean:

The mean was added as a second measure of the accuracy of the gamma distribution model. The mean represents the theoretical center of mass for the front and should always be near 1 column volume unless there are other factors in the system that cause it to shift, such as large extra column volume or interaction between the mobile phase and resin. The mean values for both equilibration and wash fronts are roughly normally distributed and do not need transformation, see FIG. 11 and FIG. 12. The mean for the equilibration front is tightly distributed around 1.07 CV with some outliers present on either side and approaching 1.2 on the high side, see FIG. 17. The wash front shows slightly more variation and is centered at 0.99 CV with several low outliers approaching 0.8, see FIG. 22. It is recommended to apply control limits of 0.80 to 1.20 CV for the mean for both fronts (see Table 2). This is appropriate because the mean is not a measure of the column performance but is used as a check to ensure that the analysis was appropriate. The tighter control limits would result in unnecessary sensitivity for this check.

TABLE 2

Recommended HETP, SS, and Mean Control Limits for Protein A Column Purification during REMICADE ® (infliximab) Manufacturing

| Front | Parameter | UCL | LCL |
|---|---|---|---|
| Equilibration | HETP | 0.243 | 0.027 |
| | SS | 0.050 | NA |
| | Mean | 1.20 | 0.80 |
| Wash | HETP | 0.352 | 0.011 |
| | SS | 0.989 | NA |
| | Mean | 1.20 | 0.80 |

Example 2—Application of the Gamma Distribution Transition Analysis for Detection of Sub-Optimal Performance of Protein a Chromatography Columns Used in to REMICADE® (Infliximab) Manufacturing The manufacturing process of the therapeutic antibody, REMICADE® (infliximab), involves several stages, four of which involve chromatography purification. The gamma distribution transition analysis (GDTA) for column qualification was applied to two or three transitions during each of these column steps. This Example describes the application of the GDTA method to the Protein A column purification step employed REMICADE® (infliximab) manufacturing. The purification process includes two transition fronts, i.e., equilibration and intermediate wash, that are appropriate for GDTA as described herein.

The GDTA was executed on 45 Equilibration fronts from the consecutive purification of 45 batches of REMICADE® (infliximab), comprising 23 batches processed on column pack 883333M001 and 22 batches processed on column pack 885473M001. The gamma front distribution analysis was performed concurrently with manufacturing and did not impact the manufacturing process. All manufacturing, monitoring and controls were performed using current, effective procedures. During the column chromatography purification of REMICADE® (infliximab), conductivity (i.e., the column outlet signal) and flow of the eluent (i.e., accumulated flow) were recorded.

Figure 32:
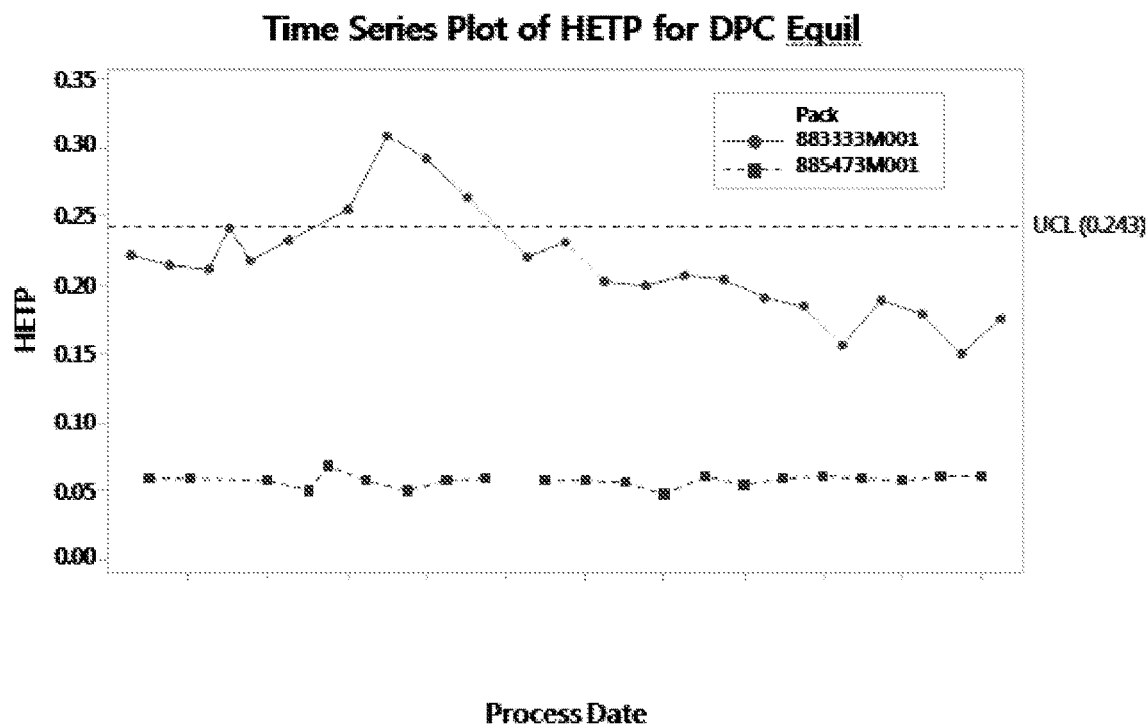
FIG. 32 is a time series plot of HETP for two different Protein A column packs as assessed over the equilibration front for 45 batches of REMICADE® (infliximab).

Trending of Equilibration HETP results for the 45 batches, see FIG. 32, showed a significant difference between column packs. Current controls for column evaluation did not identify any difference between the two column packs. Evaluation of the batch yield showed a significant (p=0.001) difference between the batches processed on the two column packs, estimated at 4.3% lower for the column pack with the higher HETP values. Other potential factors were evaluated and showed no correlation to the yield difference. Thus, the conclusion from this analysis is that the column performance difference caused lower yield. Based on this finding, the lower yielding column was conditioned to improve column packing before continued use. This example demonstrates the sensitivity of the GDTA method in assessing chromatography column quality.

Example 3—Application of the Gamma Distribution Transition Analysis for Column Qualification of SP-Sepharose High Performance Chromatography Columns Used in to REMICADE® (Infliximab) Manufacturing Overview:

As discussed above, the manufacturing process of REMICADE® (infliximab) involves several stages, four of which involve chromatography purification. This Example describes the application of the GDTA method to the SP-Sepharose High Performance (SPHP) column purification step employed REMICADE® (infliximab) manufacturing. The SPHP column is a cation exchange chromatography column. The purification process includes three transition fronts, i.e., equilibration, WFI flush, and storage fronts, that are appropriate for GDTA as described herein.

The GDTA was executed on 69 fronts from the purification of 23 batches of REMICADE® (infliximab), comprising 23 equilibration, WFI flush, and storage fronts. The gamma front distribution analysis was performed concurrently with manufacturing and did not impact the manufacturing process. All manufacturing, monitoring and controls were performed using current, effective procedures. During the column chromatography purification of REMICADE® (infliximab), conductivity (i.e., the column outlet signal) and flow of the eluent (i.e., accumulated flow) were recorded.

In addition to the application of the GDTA to column operation in real time, historical data for 189 transition fronts processed over the course of the four previous years was also collected and analyzed as described herein. The data set included 64 equilibration fronts, 63 WFI flush fronts, and 62 storage fronts. This data set was selected to provide an even distribution through the life of the columns and represents 6 column packs.

The GDTA for the SPHP column fronts was carried out as described in Example 1 above. This analysis produced measurements for HETP, SS and mean for each front. Control limits that were derived for each of these three parameters based on statistical evaluation are listed in Table 3 below.

Figure 33:
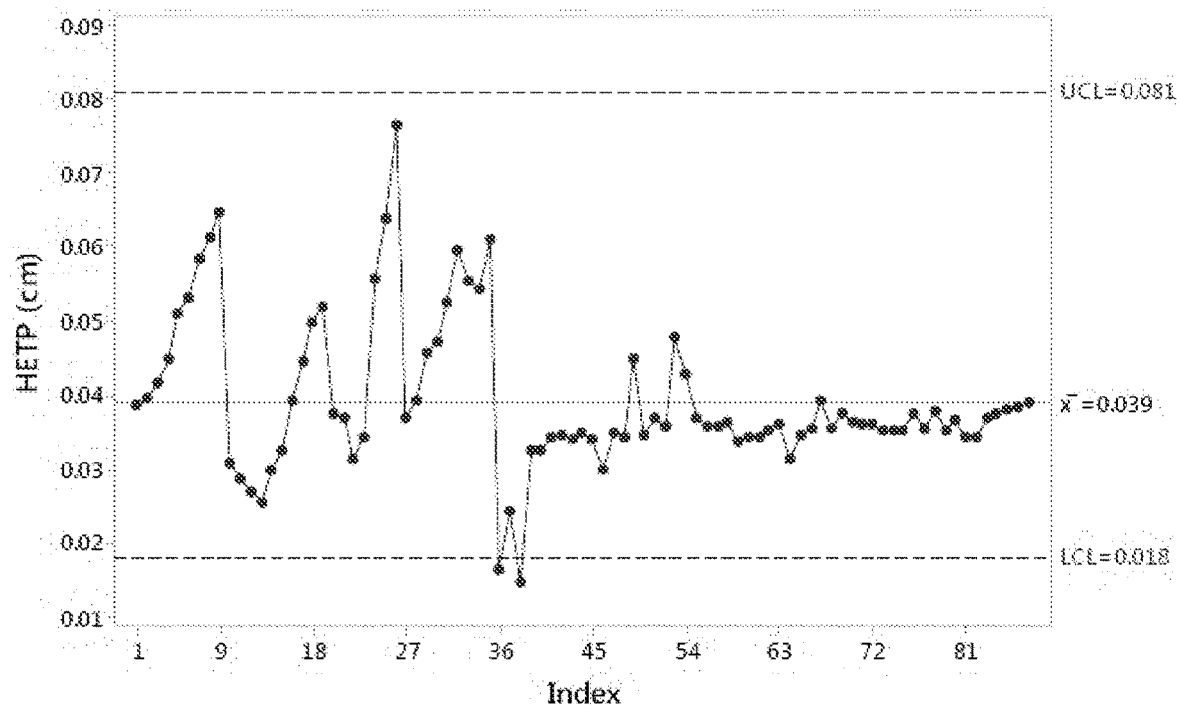
FIG. 33 is a time series plot of HETP for SP-Sepharose High Performance (SPHP) column equilibration front. Control limits are derived from the natural log Box-Cox transformation data.
Figure 34:
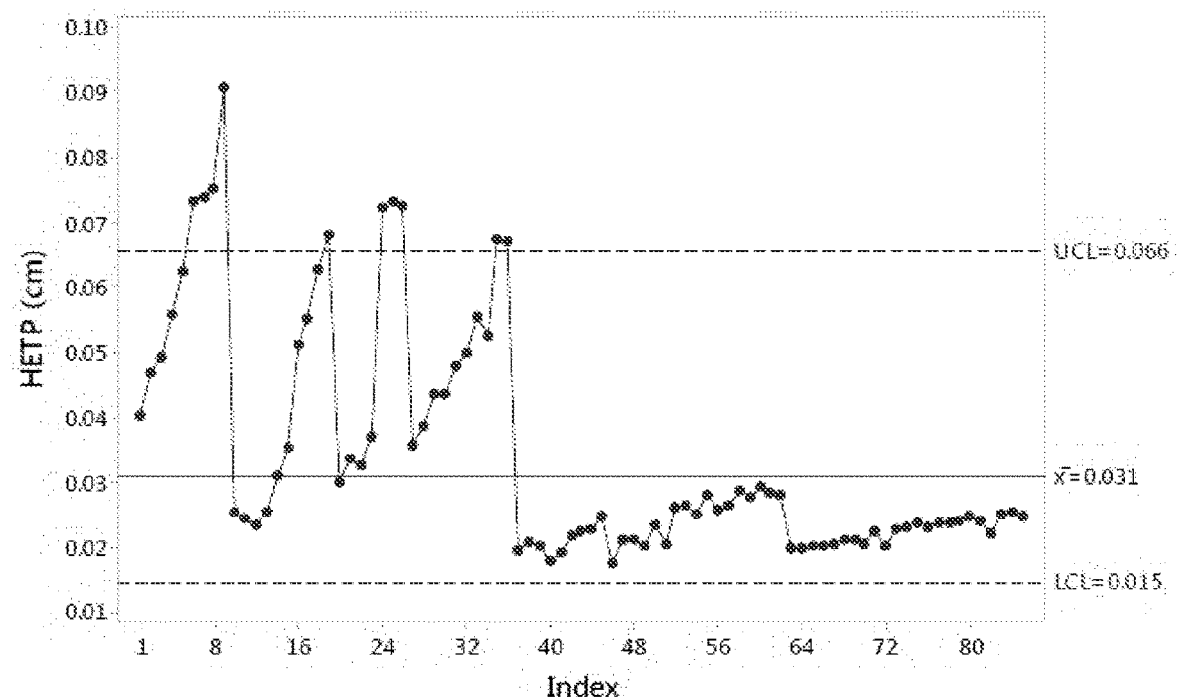
FIG. 34 is a time series plot of HETP for SPHP column WFI flush front. Control limits are derived from the natural log Box-Cox transformation data.
Figure 35:
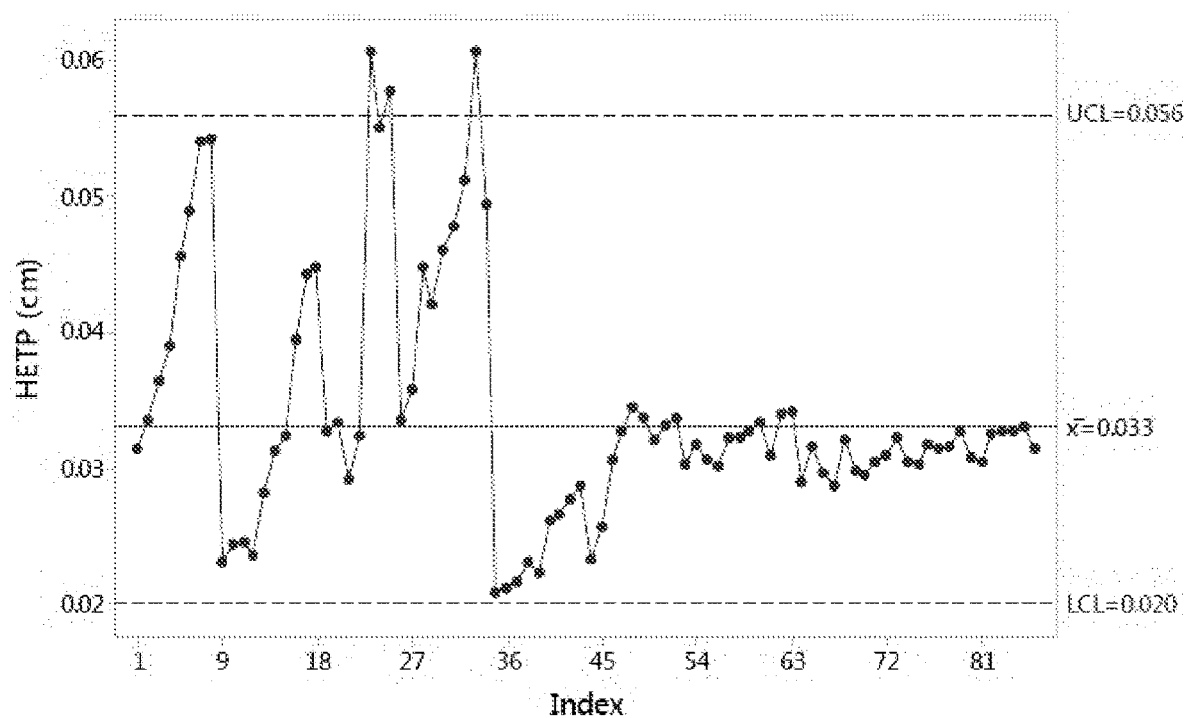
FIG. 35 is a time series plot of HETP for SPHP column storage front. Control limits are derived from the natural log Box-Cox transformation data.

Control Limits for SPHP Column:
HETP:

HETP is directly related to the column performance and is also affected by other factors in the system that may increase dispersion. The result must be >0. The control limits for HETP are best determined by using the natural log Box-Cox transformation ($\lambda=0$). The control limits for the transformed data were calculated by Minitab using the mean+/−3 standard deviations. Standard deviation is determined based on the average moving range. A moving range of 25 was selected to account for the variation in column performance over the column life. The upper and lower control limits are reverse transformed ($e^x$) to determine the control limits for the untransformed data. A time series plot for each front's HETP results and control limits is shown in FIG. 33 (equilibration front), FIG. 34 (WFI flush front), and FIG. 35 (storage front). Operation within these limits is expected to produce acceptable chromatographic performance based on this historical review. Values above the upper control limits may indicate column flow issues and should be evaluated further. Values below the lower control limits may be indicative of a calculation error.

Sum of Squares (SS):

The SS is a measure of how well the gamma distribution model fits the data. This measure will be used to ensure that HETP values calculated using the GDTA method represent the process data. There is no lower limit and the result must be >0. The upper control limit for SS is best determined by using the natural log Box-Cox transformation ($\lambda=0$). The control limits for the transformed data was calculated by Minitab using the mean+/−3 standard deviations. Standard deviation is determined based on the average moving range. A moving range of 100 was selected to account for the variation in column performance over the column life. The upper control limits for the transformed data were reverse transformed to give 0.110 for the equilibration front, 0.027 for the WFI flush front, and 0.073 for the storage front (see Table 3). Results within the limits will ensure that the model fits the data as well as historical results. If the result is outside of this range, a special cause is likely.

Mean:

The mean was added as a second measure of the accuracy of the gamma distribution model. The mean represents the theoretical center of mass for the front and should always be near 1 column volume unless there are other factors in the system that cause it to shift, such as large extra column volume or interaction between the mobile phase and resin. The mean values for equilibration, WFI flush and storage fronts have an irregular distribution and do not benefit from transformation. It is recommended to apply control limits of 0.80 to 1.20 CV for the mean for each of the fronts (see Table 3). This is appropriate because the mean is not a measure of the column performance but is used as a check to ensure that the analysis was appropriate. These limits are expected to be sufficient to identify significant departures from the expected calculation results. Tighter control limits would result in unnecessary sensitivity for this check, which is seen to vary with each column pack.

TABLE 3

Recommended HETP, SS, and Mean Control Limits for SPHP Column Purification during REMICADE ® (infliximab) Manufacturing

| Front | Parameter | UCL | LCL |
|---|---|---|---|
| Equilibration | HETP | 0.081 | 0.018 |
|  | SS | 0.110 | NA |
|  | Mean | 1.20 | 0.80 |
| WFI Flush | HETP | 0.066 | 0.015 |
|  | SS | 0.027 | NA |
|  | Mean | 1.20 | 0.80 |
| Wash | HETP | 0.056 | 0.020 |
|  | SS | 0.073 | NA |
|  | Mean | 1.20 | 0.80 |

Example 4—Application of the Gamma Distribution Transition Analysis for Column Qualification of Q2 Chromatography Columns Used in to REMICADE® (Infliximab) Manufacturing Overview:

This Example describes the application of the GDTA method to the Secondary Anion Exchange (Q2) column purification step employed REMICADE® (infliximab) manufacturing. The Q2 column is an anion exchange chromatography column. The purification process includes three transition fronts, i.e., equilibration, strip, and storage fronts, which are appropriate for GDTA as described herein.

The GDTA was executed on 68 fronts, comprising 23 equilibration and strip fronts, and 22 storage fronts. The gamma front distribution analysis was performed concurrently with manufacturing and did not impact the manufacturing process. All manufacturing, monitoring and controls were performed using current, effective procedures. During the column chromatography purification of REMICADE® (infliximab), conductivity (i.e., the column outlet signal) and flow of the eluent (i.e., accumulated flow) were recorded.

In addition to the application of the GDTA to column operation in real time, historical data for 324 transition fronts processed over the course of the four previous years was also collected and analyzed as described herein. The data set included 121 equilibration fronts, 124 strip fronts, and 79 storage fronts. This data set was selected to provide an even distribution through the life of the columns and represents 10 column packs.

The GDTA for the Q2 column fronts was carried out as described in Example 1 above. This analysis produced measurements for HETP, SS and mean for each front. Control limits that were derived for each of these three parameters based on statistical evaluation listed in Table 4 below.

Control Limits for Q2 Column:
HETP:

HETP is directly related to the column performance and is also affected by other factors in the system that may increase dispersion. The result must be >0. The control limits for HETP are best determined by using the natural log Box-Cox transformation ($\lambda=0$). The control limits for the transformed data were calculated by Minitab using the mean+/−3 standard deviations. Standard deviation is determined based on the average moving range. A moving range of 100 was selected to account for the variation in column performance over the column life. The upper and lower control limits are reverse transformed ($e^x$) to determine the control limits for the untransformed data.

Figure 36:
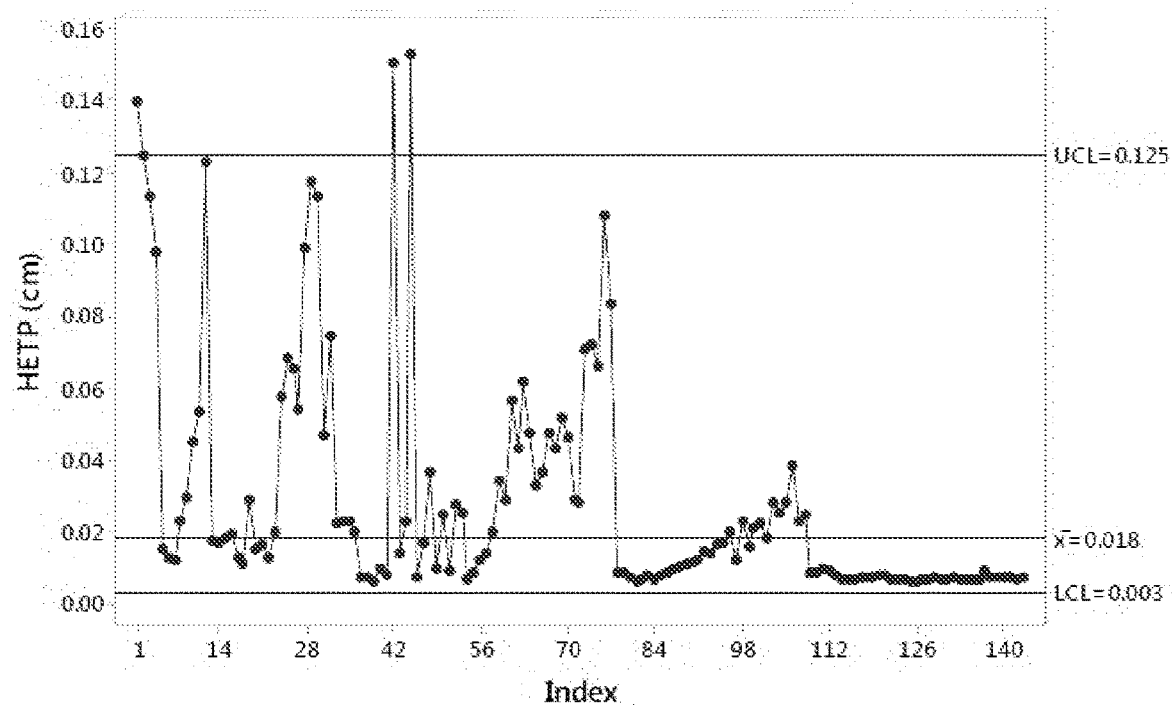
FIG. 36 is a time series plot of HETP for Q2 column equilibration front. Control limits are derived from the natural log Box-Cox transformation data.
Figure 37:
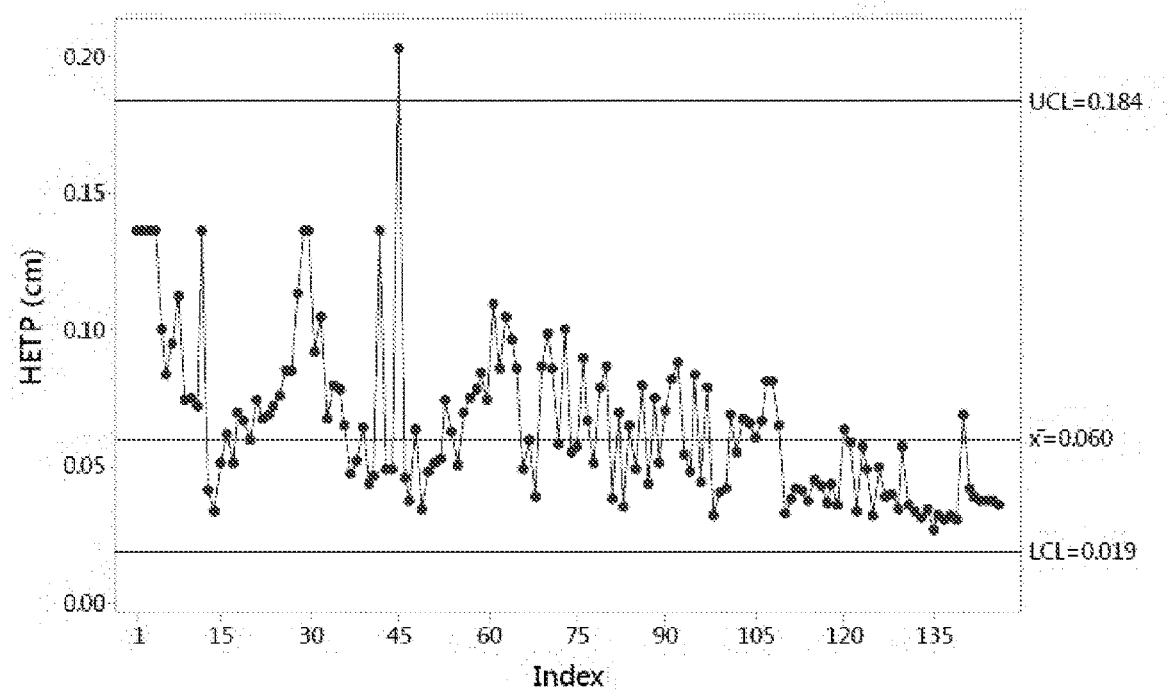
FIG. 37 is a time series plot of HETP for Q2 column strip equilibration front. Control limits are derived from the natural log Box-Cox transformation data.
Figure 38:
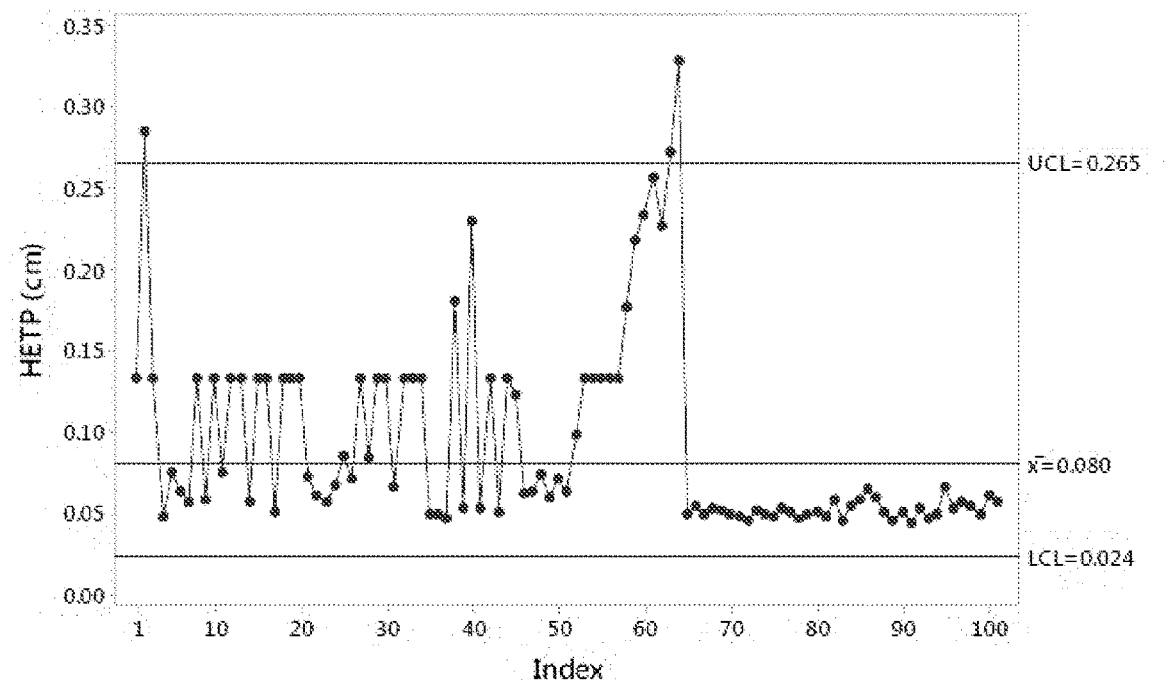
FIG. 38 is a time series plot of HETP for Q2 column storage front. Control limits are derived from the natural log Box-Cox transformation data.

A time series plot for each front's HETP results and control limits is shown in FIG. 36 (equilibration front), FIG. 37 (strip front), and FIG. 38 (storage front). Operation within these limits is expected to produce acceptable chromatographic performance based on this historical review. Values above the upper control limits may indicate column flow issues and should be evaluated further. Values below the lower control limits may be indicative of a calculation error.

Sum of Squares (SS):

The SS is a measure of how well the gamma distribution model fits the data. This measure will be used to ensure that HETP values calculated using the GDTA method represent the process data. There is no lower limit and the result must be >0. The upper control limit for SS is best determined by using the natural log Box-Cox transformation ($\lambda$=0). The control limits for the transformed data were calculated by Minitab using the mean+/−3 standard deviations. Standard deviation is determined based on the average moving range. A moving range of 100 was selected to account for the variation in column performance over the column life. The standard deviation was determined from the aggregate data for the Storage front, as the moving range method produced a higher standard deviation. The control limits are reported in Table 4 below. Results within the limits will ensure that the model fits the data as well as historical results. If the result is outside of this range, a special cause is likely.

Mean:

The mean was added as a second measure of the accuracy of the gamma distribution model. The mean represents the theoretical center of mass for the front and should always be near 1 column volume unless there are other factors in the system that cause it to shift, such as large extra column volume or interaction between the mobile phase and resin. The mean values for equilibration, strip, and storage fronts have an irregular distribution and do not benefit from transformation. It is recommended to apply control limits of 0.80 to 1.20 CV for the mean for each of the fronts (see Table 4). This is appropriate because the mean is not a measure of the column performance but is used as a check to ensure that the analysis was appropriate. These limits are expected to be sufficient to identify significant departures from the expected calculation results. Tighter control limits would result in unnecessary sensitivity for this check, which is seen to vary with each column pack.

TABLE 4

Recommended HETP, SS, and Mean Control Limits for Q2 Column Purification during REMICADE ® (infliximab) Manufacturing

| Front | Parameter | UCL | LCL |
|---|---|---|---|
| Equilibration | HETP | 0.125 | 0.003 |
|  | SS | 0.344 | NA |
|  | Mean | 1.20 | 0.80 |
| Strip | HETP | 0.184 | 0.019 |
|  | SS | 0.156 | NA |
|  | Mean | 1.20 | 0.80 |
| Wash | HETP | 0.265 | 0.024 |
|  | SS | 0.691 | NA |
|  | Mean | 1.20 | 0.80 |

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of operating a chromatography column, said method comprising:
   collecting a column outlet signal and accumulated flow parameters at two or more intervals of at least one mobile phase transition front during a first operation of the chromatography column comprising column packing;
   determining a model gamma cumulative distribution curve based on the collected column outlet signal and accumulated flow parameters for the at least one mobile phase transition front using Formula Ia for a rising transition front or Formula Ib for a falling transition front, $$C = 1 - \frac{1}{\Gamma(k)}\gamma\left(k, \frac{V - V_i}{\theta}\right) \qquad \text{Formula Ia}$$

or $$C = \frac{1}{\Gamma(k)}\gamma\left(k, \frac{V - V_i}{\theta}\right) \qquad \text{Formula Ib}$$

wherein C is the column outlet signal for a given V, V is the accumulated flow divided by the column volume, and k, $\theta$, and Vi are the shape, scale, and offset parameters, respectively, used to define the curve;

calculating a height equivalent theoretical plate (HETP) value for the at least one mobile phase transition front using Formula II and the model gamma cumulative distribution curve parameters of k, $\theta$, and Vi, $$HETP = \frac{\sigma^2}{\mu^2}L \qquad \text{Formula II}$$

wherein $\mu = k\theta + V_i$ $\sigma = \sqrt{k\theta^2}$

L = column length; and assessing the quality of the chromatography column packing based on said calculated HETP value.

2. The method of claim 1, further comprising: conditioning, replacing, or repacking the chromatography column based on said assessing.

3. The method of claim 2 further comprising: collecting column outlet signals and accumulated flow parameters at two or more intervals of a corresponding mobile phase transition front during one or more subsequent uses of the chromatography column packing;
   performing said determining and said calculating using the column outlet signal and accumulated flow parameters collected during each of the one or more subsequent uses of the chromatography column packing;
   determining an HETP value of the chromatography column packing during each of said one or more subsequent uses based on said performing;
   compiling a trend of the determined HETP values of the chromatography column packing of the one or more subsequent uses; and
   identifying a change in the quality of the chromatography column packing based on said compiled trend, wherein said conditioning, replacing, or repacking of the chromatography column is based on said identifying.

4. The method of claim 3, wherein an increase in the HETP value of the chromatography column packing in the one or more subsequent uses of said column packing as compared to the HETP value of the chromatography column packing in one or more earlier uses of said column packing identifies a decrease in the quality of the chromatography column packing.

5. The method of claim 2, wherein column outlet signals and accumulated flow parameters of two or more different mobile phase transition fronts during said first operation of the column packing are collected, said method comprising:
   performing said determining and calculating using the column outlet signal and accumulated flow parameters collected for each of the two or more different mobile phase transition fronts independently to calculate an HETP value for each of the two of more different mobile phase transition fronts;
   assessing the quality of the chromatography column packing based on the two or more calculated HETP values, whereby said conditioning, replacing, or repacking of the chromatography column is based on said assessing.

6. The method of claim 1, wherein the mobile phase transition front is generated by a change from a mobile phase containing a denaturing agent to a mobile phase containing a non-denaturing agent.

7. The method of claim 1, wherein the mobile phase transition front is generated by a change from a mobile phase containing a non-denaturing agent to a mobile phase containing a denaturing agent.

8. The method of claim 1, wherein the mobile phase transition front is generated by a change from an alkaline mobile phase condition to a more acidic mobile phase condition.

9. The method of claim 1, wherein the mobile phase transition front is generated by a change from an acidic mobile phase condition to a more alkaline mobile phase condition.

10. The method of claim 1, wherein the mobile phase transition front is generated by a change from an organic solvent containing mobile phase to an aqueous mobile phase.

11. The method of claim 1, wherein the mobile phase transition front is generated by a change from an aqueous mobile phase to an organic solvent containing mobile phase.

12. The method of claim 1, wherein the column outlet signal is conductivity.

13. The method of claim 1, wherein said determining comprises:
   normalizing said collected column outlet signal of the mobile phase transition front by setting the minimum signal value to 0 and the maximum conductivity value to 1.

14. The method of claim 1, wherein said collecting comprises:
   adding a first mobile phase to the chromatography column containing said column packing;
   adding a second mobile phase to the chromatography column containing said column packing, wherein said first and second mobile phases have different detectable column outlet signals; and
   collecting said column outlet signal and accumulated flow parameters at two or more intervals of the mobile phase transition between the first and second mobile phases.

15. The method of claim 14, wherein the column outlet signal for the first and second mobile phases differ in signal by an amount exceeding the signal noise.

16. The method of claim 1, wherein the column outlet signal and accumulated flow parameters are collected at various intervals throughout the entirety of the mobile phase transition front.

17. The method of claim 1, wherein the chromatography column packing is selected from the group consisting of affinity chromatography packing material, ion exchange chromatography packing material, adsorption chromatography packing material, hydrophobic interaction chromatography packing material, metal chelate affinity chromatography packing material, size exclusion chromatography packing material, and molecular exclusion chromatography packing material.

* * * * *